US011535824B2

(12) United States Patent
Chung et al.

(10) Patent No.: US 11,535,824 B2
(45) Date of Patent: Dec. 27, 2022

(54) NUCLEAR TRANSFER

(71) Applicant: Sung Kwang Medical Foundation, Seoul (KR)

(72) Inventors: Young Gie Chung, Shrewsbury, MA (US); Dong Ryul Lee, Seoul (KR); Jin Hee Eum, Seoul (KR)

(73) Assignee: Sung Kwang Medical Foundation, Seoul (KR)

( * ) Notice: Subject to any disclaimer, the term of this patent is extended or adjusted under 35 U.S.C. 154(b) by 0 days.

(21) Appl. No.: 15/338,144

(22) Filed: Oct. 28, 2016

(65) Prior Publication Data

US 2017/0204369 A1  Jul. 20, 2017

Related U.S. Application Data

(60) Provisional application No. 62/247,903, filed on Oct. 29, 2015.

(51) Int. Cl.
| *C12N 5/074* | (2010.01) |
| *C12N 15/873* | (2010.01) |
| *C12N 15/877* | (2010.01) |
| *C12N 5/073* | (2010.01) |
| *C12N 5/075* | (2010.01) |

(52) U.S. Cl.
CPC ......... *C12N 5/0607* (2013.01); *C12N 5/0604* (2013.01); *C12N 5/0609* (2013.01); *C12N 15/873* (2013.01); *C12N 15/8775* (2013.01); *C12N 2501/065* (2013.01); *C12N 2501/602* (2013.01); *C12N 2501/603* (2013.01); *C12N 2501/604* (2013.01); *C12N 2501/606* (2013.01); *C12N 2501/608* (2013.01); *C12N 2510/04* (2013.01); *C12N 2517/04* (2013.01)

(58) Field of Classification Search
CPC ...... C12N 5/0607; C12N 5/12; C12N 15/873; C12N 15/8775; C12N 2501/602; C12N 2501/603; C12N 2501/604; C12N 2501/606; C12N 2501/608; C12N 2501/65; C12N 2506/04; C12N 2510/04; C12N 5/0609; C12N 2501/065; C12N 2517/04; C12N 5/0604
USPC .................. 435/325, 375, 404, 193
See application file for complete search history.

(56) References Cited

U.S. PATENT DOCUMENTS

| 10,017,733 | B2 | 7/2018 | Chung et al. |
| 11,339,369 | B2 | 5/2022 | Chung et al. |
| 2004/0091936 | A1 | 5/2004 | West |
| 2008/0299091 | A1 | 12/2008 | Revazova et al. |
| 2012/0083032 | A1 | 4/2012 | Roh et al. |
| 2012/0184466 | A1 | 7/2012 | Revazova et al. |
| 2014/0234968 | A1* | 8/2014 | Chung ............... C12N 5/0606 435/449 |
| 2018/0282688 | A1 | 10/2018 | Chung et al. |

FOREIGN PATENT DOCUMENTS

| AU | 2014217550 A1 | 10/2015 |
| AU | 2017272196 A1 | 1/2018 |
| CN | 1922307 A | 2/2007 |
| CN | 101525592 A | 9/2009 |
| CN | 101535468 A | 9/2009 |
| CN | 105209606 A | 12/2015 |
| CN | 109797134 A | 5/2019 |
| EP | 2956542 A1 | 12/2015 |
| JP | 2005-510232 A | 4/2005 |
| JP | 2007-516720 A | 6/2007 |
| JP | 2009-512450 A | 3/2009 |
| JP | 2016510220 A | 4/2016 |
| JP | 2018046839 A | 3/2018 |
| KR | 20150122688 A | 11/2015 |
| WO | WO 2003/046141 A2 | 6/2003 |
| WO | WO 2003/100018 A2 | 12/2003 |
| WO | WO 2007/047979 A2 | 4/2007 |
| WO | WO 2008/013557 A1 | 1/2008 |
| WO | WO 2008/124142 A1 | 10/2008 |
| WO | WO 2009/015036 A1 | 1/2009 |
| WO | WO 2010/134076 A1 | 11/2010 |
| WO | WO 2012/029957 A1 | 3/2012 |
| WO | WO 2014/125363 A1 | 8/2014 |

OTHER PUBLICATIONS

Tachibana et al., Cell, 153: 1228-1238, 2013.*
Kaneda et al., Molecular Therapy, 6(20: 219-226, 2002.*
Burgstaller et al., BMC Developmental Biology 2007, 7:141.*
Boriack-Sjodin et al., Biochemistry, 55: 1557-1569, 2016.*
Torres-Padilla et al., Nature, 445(7124): 214-218, 2007.*
International Search Report and Written Opinion for International application No. PCT/IB2014/000160 dated Jun. 25, 2014.
International Preliminary Report on Patentability for International application No. PCT/IB2014/000160 dated Aug. 27, 2015.
EP 14751293.3 Extended Search Report dated Aug. 16, 2016; 9 pages.
Byrne et al., Producing Primate Embryonic Stem Cells by Somatic Cell Nuclear Transfer, Nature, 2007, vol. 450, pp. 497-502.
Chen et al., Progress in the Studies of Parthenogenetic Embryonic Stem Cells, 2004, National Journal of Andrology, vol. 1(1), pp. 55-58.
Chung et al., Human Somatic Cell Nuclear Transfer Using Adult Cells, Cell Stem Cells, 2014, vol. 14, pp. 1-4.

(Continued)

*Primary Examiner* — Anne Marie S Wehbe
(74) *Attorney, Agent, or Firm* — Nixon Peabody LLP; Linda B. Huber

(57) ABSTRACT

The present invention provides methods and compostions to improve the efficiency of somatic cell nuclear transfer (SCNT). There is increasing evidence that the epigenetic state of donor nuclei has a significant impact on potential of nuclear transfer embryos to develop into blastocysts, from which pluripotent stem cells are derived. Strategic application of histone agents, capable of altering epigenetic state such as methylation, allows zygotic activation and robust blastocyst generation.

12 Claims, 3 Drawing Sheets

(56) References Cited

OTHER PUBLICATIONS

Fan et al, Derivation of Cloned Human Blastocysts by Histone Deacetylase Inhibitor Treatment after Somatic Cell Nuclear Transfer with ß-Thaassemia Fibroblasts, Stem Cells and Development, 2011, vol. 20(11), pp. 1951-1959.
Ju et al., Establishment of Stem Cell Lines from Nuclear Transferred and Parthenogenetically Activated Mouse Oocytes for Therapeutic Cloning, Fertility and Sterility, 2008, vol. 89(3), pp. 1314-1323.
Kishigami et al., Significant improvement of mouse cloning technique by treatment with trichostatin A after somatic nuclear transfer, Biomedical and Biophysical Research Communication, 2006, vol. 340, pp. 183-189.
Liu et al., Genetic and epigenetic X-chromosome variations in a parthenogenetic human embryonic stem cell line, Journal of Assisted Reproduction and Genetics, 2011, vol. 28(4), pp. 303-313.
Mai et al., Derivation of human embryonic stem cell lines from parthenogenetic blastocysts, Cell Research, 2007, vol. 17, pp. 1008-1019.
Matsuura et al., P34cdc2 Kinase and MAP Kinase Activities and Parthenogenetic Activation in Porcine Oocytes after Injection of Miniature Pig Sperm Extracts, J Mamm Ova Res, 2008, vol. 25, pp. 63-68.
Noggle et al., Human Oocytes Reprogram Somatic Cells to a Pluripotent State, Nature, 2011, vol. 478, pp. 70-77.
Nasr-Esfahani et al., Artificial Oocyte Activation and Intracytoplasmic Sperm Injection, Fertility & Sterility, 2010, vol. 94(2), pp. 520-526.
Okada et al. Activation and Development of Pig Oocytes after Microinjection of Crude Sperm Extract, J Mamm Ova Res, 2004, vol. 21, pp. 134-140.
Ping et al., Analysis of International Development Trend of Stem Cell Research, International Development of Stem Cells, Science Focus, 2011, vol. 6(2), Abstract only.
Rideout et al., Correction of a Genetic Defect by Nuclear Transplantation and Combined Cell and Gene Therapy, Cell, 2002, vol. 109, pp. 17-27.
Rybouchkin et al., Role of histone acetylation in reprogramming of somatic nuclei following nuclear transfer, Biology of Reproduction, 2006, vol. 74, pp. 1083-1089.
Tachibana et al. Human Embryonic Stem Cells Derived by Somatic Cell Nuclear Transfer, Cell, 2013, vol. 153, pp. 1-11.
Takahashi et al., Induction of Pluripotent Stem Cells from Adult Human Fibroblasts by Defined Factors, Cell, 2007, vol. 131, pp. 861-872.
Torres-Padilla et al., Histone arginine methylation regulates pluripotency in the early mouse embryo, Nature, 2007, vol. 445(7124), pp. 214-218.
Wakayama et al., Differentiation of Embryonic Stem Cell Lines Generated from Adult Somatic Cells by Nuclear Transfer, Science, 2001, vol. 292, pp. 740-743.
Wang et al. Caffeine can be used for Oocyte Enucleation, Cellular Reprogramming, 2011, vol. 13(3), pp. 225-232.
Wu et al. CARM1 is required in embryonic stem cells to maintain pluripotency and resist differentiation, Stem Cells, 2009, vol. 27(11), pp. 2637-2645.
Dominguez-Bendala et al., Islet Cell Therapy and Pancreatic Stem Cells, Handbook of Stem Cells, Chapter 70, 2013, pp. 835-853.
Lai et al., SRY (Sex Determining Region Y)-box-2 (Sox2)/Poly ADP-Ribose Polymerase 1 (Parp1) Complexes Regulate Pluripotency, PNAS, 2012, vol. 109(10), pp. 3772-3777.
Mallon et al., Comparison of the Molecular Profiles of Human Embryonic and Induced Pluripont Stem Cells of Isogenic Origin, Stem Cells Res., 2014, vol. 12(2), pp. 376-386.
Reijo-Pera et al., Gene Expression Profiles of Human Inner Cell Mass Cells and Embryonic Stem Cells, Differentiation, 2009, vol. 78, pp. 18-23.
Reubinoff et al., Embryonic Stem Cell Lines from Human Blastocysts: Somatic Differentiation in Vitro, Nature Biotechnology, 2000, vol. 18, pp. 399-404.
Thomson et al., Embryonic Stem Cell Lines Derived from Human Blastocysts, Science, 1998, vol. 282, pp. 1145-1147.
UK House of Parliaments Select Committee on Science Technology, Government Proposals for the Regulation of Hybrid and Chimera Embryos, Fifth Report of Session, 2006-2007, vol. 2, pp. 76-80.
Yu et al., Histone Methyltransferases as Therapeutic Targets for Kidney Diseases, Frontiers in Pharmacology, 2019, pp. 1-11.
Jo et al., Regulation of Differentiation Potential of Human Mesenchymal Stem Cells by Intracytoplasmic Delivery of Coactivator-Associated Arginine Methyltransferase 1 Protein Using Cell-Penetrating Peptide, Stem Cells, 2012, vol. 30, pp. 1703-1713.
Jo et al., Cell-penetrating peptide (CPP)-conjugated proteins is an efficient tool for manipulation of human mesenchymal stromal cells, Scientific Reports, 2014, pp. 1-8.
Yang et al., Effect of cell-penetrating peptide-conjugated estrogen-related receptor B on the development of mouse embryos cultured in vitro, Clin Exp Reprod Med, 2014, vol. 41(1), pp. 1-8.
Yang et al., Supplementation With Cell-Penetrating Peptide-Conjugated Estrogen-Related Receptor B Improves the Formation of the Inner Cell Mass and the Development of Vitrified/Warmed Mouse Embryos, Reproductive Sciences, 2016, pp. 1-9.

\* cited by examiner

NUCLEAR TRANSFER

CROSS-REFERENCE TO RELATED APPLICATIONS

This application claims the benefit of U.S. provisional patent application No. 62/247,903 filed Oct. 29, 2015.

FIELD OF THE INVENTION

The invention relates to immunocompatible pluripotent stem cells (pSCs), including patient-specific pSCs. Described herein are compositions and methods related to nuclear transfer for application in regenerative medicine therapies.

BACKGROUND

Human pluripotent stem cells (hPSCs) possess the remarkable ability to differentiate into virtually all somatic cell types in the body (pluripotency), while maintaining proliferative capacity in an undifferentiated state (self-renewal). These unique features of hPSCs provide opportunity to generate transplantable cells and tissue material for treatment of diseases and conditions. Many human injuries and diseases result from cellular defects, including those of a single cell type. Replacement with appropriate stem cells, progenitor cells, or in vitro differentiated cells, could lead to novel therapeutic approaches in the clinic. The self-renewal capacity of pluripotent stem cells further provides a near limitless resource of transplantable material. Generation of hPSCs in a patient-specific manner, thereby leads to therapeutic approaches that eliminate reduce risk of immunological rejection and tolerance.

One strategy for generation of immunocompatible hPSCs is patient-specific hPSCs derived through somatic cell nuclear transfer (SCNT). Somatic cell nuclear transfer involves isolation of the nucleus of a somatic cell of a donor patient and insertion into an enucleated recipient oocyte. Transfer of the donor nucleus to the recipient oocyte's cytoplasm results in reprogramming of the transferred donor nucleus through silencing of somatic cell genes and activation of embryonic genes. From these reconstructed oocytes, one can establish blastocysts in culture to isolate hPSCs from the inner cell mass (ICM). As the result of nuclear transfer the hPSCs (NT-hPSCs), the resulting cells generated from their development carry the nuclear genetic material of the patient and are patient-specific.

Despite promising advances in SCNT techniques, there are significant limitations that, at present, preclude practical clinical application. For nuclear transfer, prior attempts led to as few as 2% of reconstructed oocytes crossing the 8-cell threshold towards blastocyst formation. While significant improvements have recently been reported, the exact mechanisms allowing for consistent blastocyst formation are presently unclear. It does appear that a key obstacle for development of SCNT embryos is zygotic gene activation (ZGA), which occurs at the 4- to 8-cell stage in large mammals such as pig, bovine and human. Based on the Inventors' previous studies wherein histone methylation altering agents could improve the rate of ZGA successful SCNT, and significance of donor variability on these processes, it appears that SCNT embryos have undefined epigenetic barriers pre-existing in the genome of donor cells. Dysregulated genes in late cleavage stage human SCNT embryos have been identified, but the full nature of the "pre-existing epigenetic barriers" and their relationship with impaired ZGA in SCNT embryos are unknown. Accordingly, there is a need to improve human SCNT cloning efficiency by identifying removing epigenetic barriers in the genome of the donor cell nuclei so that the human SCNT embryo can proceed efficiently through zygotic gene activation (ZGA) without developmental arrest.

Described herein are compositions and methods allowing for successful development through the 2-, 4- and 8-cell stage to blastocyst without developmental defects or loss of viability. By altering epigenetic state of donor nuclei, enhanced ZGA results in dramatically increased blastocyst production and generation of hPSCs.

SUMMARY OF THE INVENTION

Described herein is a method of generating a nuclear transfer human pluripotent stem cell line (NT-hPSC), including removing the nucleus of an oocyte, generating a nuclear transferred (NT) oocyte by adding at least one nucleus of at least one donor cell, activating the NT oocyte by incubation in an activation medium, generating a blastocyst from the activated NT oocyte, and isolating inner cell mass (ICM) cells from the blastocyst, wherein the ICM cells are capable of further culturing as a NT-hPSC cell line. In other embodiments, the at least one nucleus of at least one donor cell includes direct injection. In other embodiments, the at least one nucleus of at least one donor cell includes somatic cell fusion. In other embodiments, somatic cell fusion includes contact of Sendai virus, protein or extract thereof, with the at least one donor cell. In other embodiments, the at least one donor cell includes a somatic cell or germ cell. In other embodiments, the at least one nucleus of at least one donor cell is modified by contact with an agent capable of altering epigenetic status. In other embodiments, the agent capable of altering epigenetic status includes one or more of histoneacetyltransfer (HAT) proteins, histone deacetylase (HDAC) proteins, lysine demethylase domain proteins, and protein methyl transferase (PMT) domain proteins. In other embodiments, the agent includes a small interfering RNA (siRNA), small molecule, protein, peptide, or antibody. In other embodiments, the agent includes one or more of Oct3/4, Sox2, Klf4, c-Myc and/or Lin28. In other embodiments, the NT oocyte is incubated in the presence of an agent capable of altering epigenetic status. In other embodiments, the agent capable of altering epigenetic status includes histoneacetyltransfer (HAT) proteins, histone deacetylase (HDAC) proteins, lysine demethylase domain proteins, and protein methyl transferase (PMT) domain proteins. In other embodiments, the agent includes a small interfering RNA (siRNA), small molecule, protein, peptide, or antibody.

Also described herein is a nuclear transfer human pluripotent stem cell line (NT-hPSC) cell line produced by the method of claim a method of generating a nuclear transfer human pluripotent stem cell line (NT-hPSC), including removing the nucleus of an oocyte, generating a nuclear transferred (NT) oocyte by adding at least one nucleus of at least one donor cell, activating the NT oocyte by incubation in an activation medium, generating a blastocyst from the activated NT oocyte, and isolating inner cell mass (ICM) cells from the blastocyst, wherein the ICM cells are capable of further culturing as a NT-hPSC cell line. In other embodiments, the at least one nucleus of at least one donor cell includes direct injection. In other embodiments, the at least one nucleus of at least one donor cell includes somatic cell fusion. In other embodiments, somatic cell fusion includes contact of Sendai virus, protein or extract thereof, with the at least one donor cell. In other embodiments, the at least one donor cell includes a somatic cell or germ cell. In other embodiments, the at least one nucleus of at least one donor cell is modified by contact with an agent capable of altering epigenetic status. In other embodiments, the agent capable of altering epigenetic status includes one or more of histoneacetyltransfer (HAT) proteins, histone deacetylase (HDAC) proteins, lysine demethylase domain proteins, and protein methyl transferase (PMT) domain proteins. In other embodiments, the agent includes a small interfering RNA (siRNA), small molecule, protein, peptide, or antibody. In other embodiments, the agent includes one or more of Oct3/4, Sox2, Klf4, c-Myc and/or Lin28. In other embodiments, the NT oocyte is incubated in the presence of an agent capable of altering epigenetic status. In other embodiments, the agent capable of altering epigenetic status includes histoneacetyltransfer (HAT) proteins, histone deacetylase (HDAC) proteins, lysine demethylase domain proteins, and protein methyl transferase (PMT) domain proteins. In other embodiments, the agent includes a small interfering RNA (siRNA), small molecule, protein, peptide, or antibody.

Further described herein is a method of nuclear transfer including removing the host nucleus of the oocyte, generating a nuclear transferred (NT) oocyte by adding at least one nucleus of at least one donor cell to an oocyte, activating the NT oocyte by incubation in an activation medium, generating a blastocyst from the activated NT oocyte, and isolating inner cell mass (ICM) cells from the blastocyst, wherein the ICM cells are capable of further culturing as a NT-hPSC cell line, and further wherein the at least one donor cell, oocyte, NT oocyte, and/or blastocyst contacts an agent capable of altering epigenetic status. In other embodiments, contact with an agent capable of altering epigenetic status includes addition of mRNA expressing one or more of histoneacetyltransfer (HAT) proteins, histone deacetylase (HDAC) proteins, lysine demethylase domain proteins, and protein methyl transferase (PMT) domain proteins. In other embodiments, contact with an agent capable of altering epigenetic status includes culturing in the presence of a small interfering RNA (siRNA), small molecule, protein, peptide, or antibody. In other embodiments, contact with an agent capable of altering epigenetic status includes culturing in the presence of Oct3/4, Sox2, Klf4, c-Myc and/or Lin28. In other embodiments, the at least one donor cell is cultured in the presence of Oct3/4, Sox2, Klf4, c-Myc and/or Lin28 for at least 3 weeks. In other embodiments, the least one donor cell is cultured in the presence of Oct3/4, Sox2, Klf4, c-Myc and/or Lin28 for less than 3 weeks.

BRIEF DESCRIPTION OF THE FIGURES

Exemplary embodiments are illustrated in referenced figures. It is intended that the embodiments and figures disclosed herein are to be considered illustrative rather than restrictive.

DETAILED DESCRIPTION OF THE INVENTION

Figure 1:
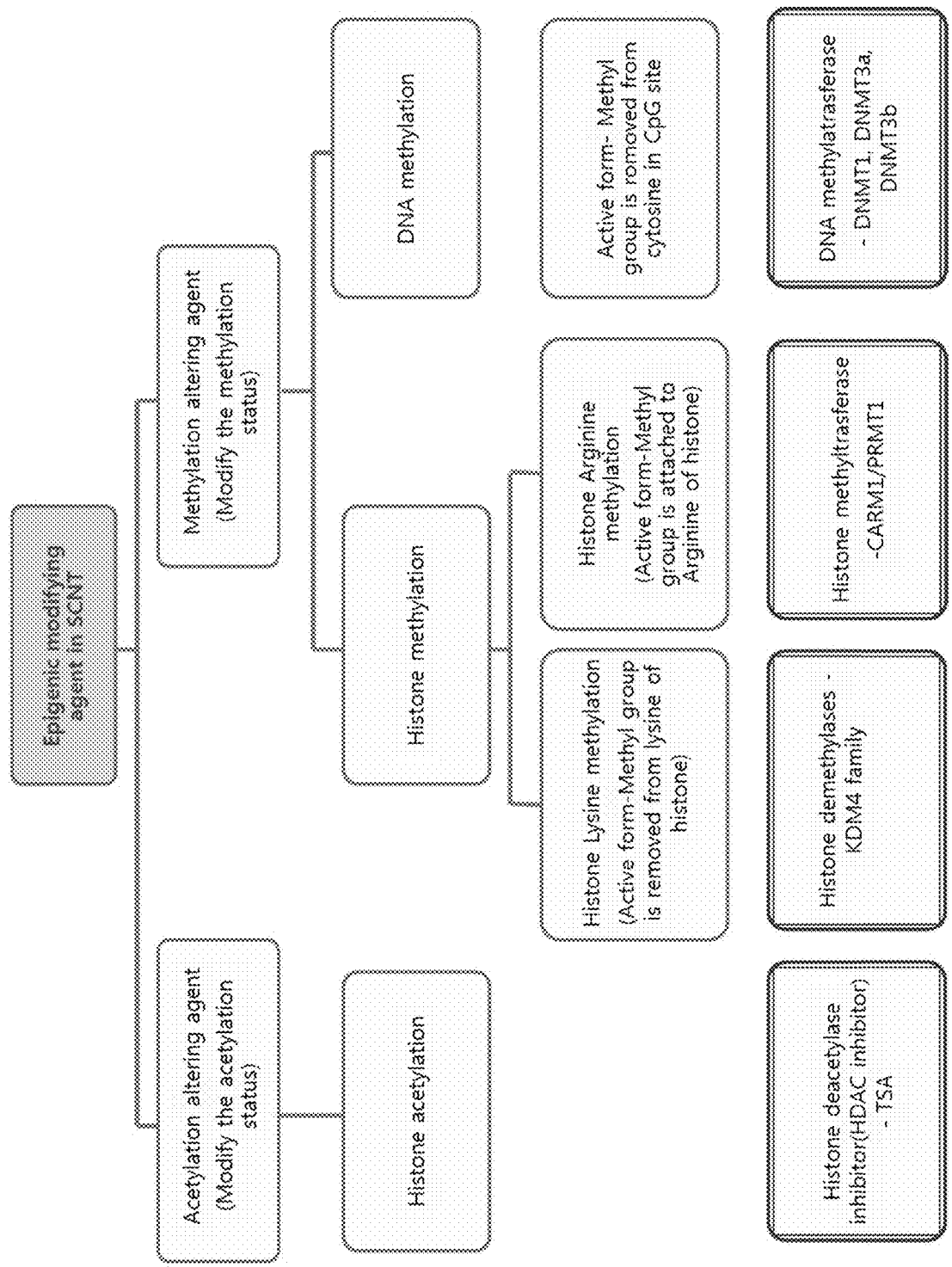
FIG. 1. Epigenetic modifying agents implicated in somatic cell nuclear transfer.
Figure 2:
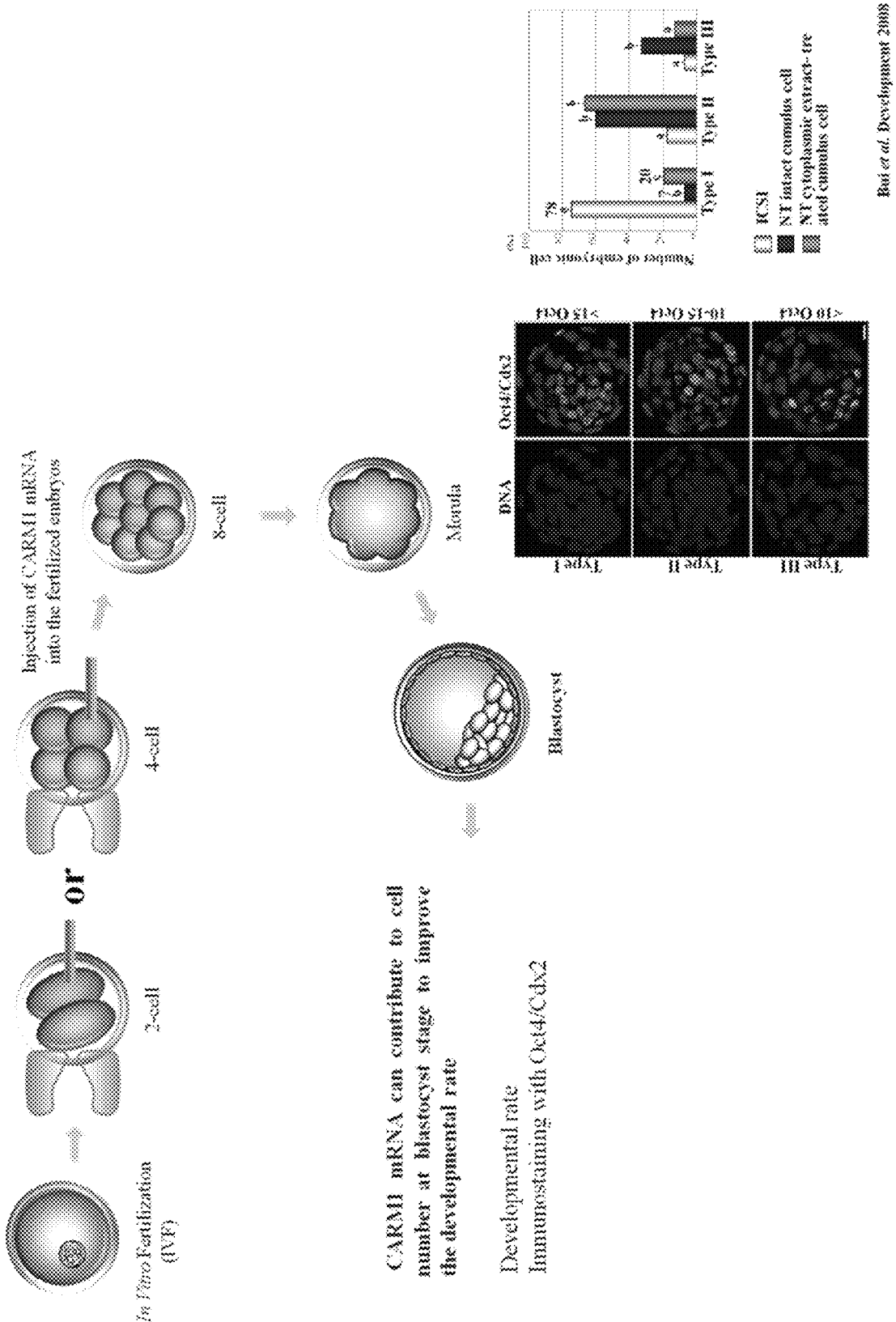
FIG. 2. Materials and methods related to injection of CARM1 to promote blastocyst development. Adapted from Bui et al. Development 2008.
Figure 3:
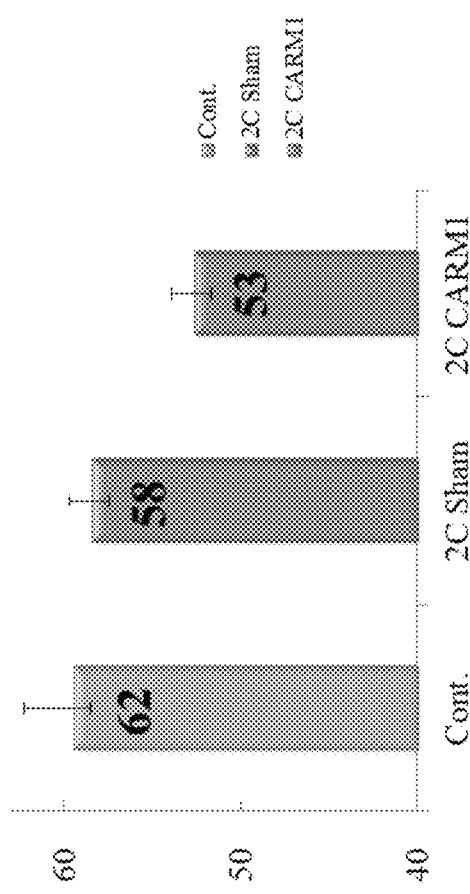
FIG. 3. Effect of CARM1 injection on inner cell mass numbers.
Figure 3:
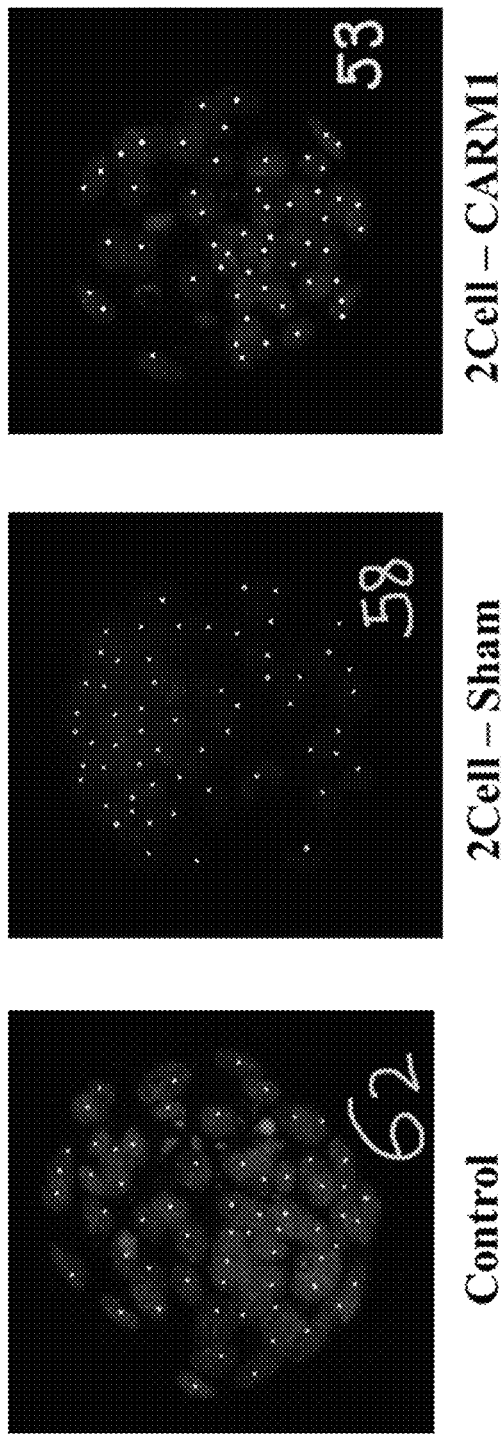

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods described herein. For purposes of the present invention, the following terms are defined below.

"Administering" and/or "administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods known in the art. Parenteral refers to a route of delivery that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

"Modulation" or "modulates" or "modulating" as used herein refers to upregulation (i.e., activation or stimulation), down regulation (i.e., inhibition or suppression) of a response or the two in combination or apart.

"Pharmaceutically acceptable carriers" as used herein refer to conventional pharmaceutically acceptable carriers useful in this invention.

"Promote" and/or "promoting" as used herein refer to an augmentation in a particular behavior of a cell or organism.

"Subject" as used herein includes all animals, including mammals and other animals, including, but not limited to, companion animals, farm animals and zoo animals. The term "animal" can include any living multi-cellular vertebrate organisms, a category that includes, for example, a mammal, a bird, a simian, a dog, a cat, a horse, a cow, a rodent, and the like. Likewise, the term "mammal" includes both human and non-human mammals.

"Therapeutically effective amount" as used herein refers to the quantity of a specified composition, or active agent in the composition, sufficient to achieve a desired effect in a subject being treated. A therapeutically effective amount may vary depending upon a variety of factors, including but not limited to the physiological condition of the subject (including age, sex, disease type and stage, general physical condition, responsiveness to a given dosage, desired clinical effect) and the route of administration. One skilled in the clinical and pharmacological arts will be able to determine a therapeutically effective amount through routine experimentation.

"Treat," "treating" and "treatment" as used herein refer to both therapeutic treatment and prophylactic or preventative measures, wherein the object is to prevent or slow down (lessen) the targeted condition, disease or disorder (collectively "ailment") even if the treatment is ultimately unsuccessful. Those in need of treatment may include those already with the ailment as well as those prone to have the ailment or those in whom the ailment is to be prevented.

As described, isolation and characterization of human pluripotent stem cells (hPSCs) and breakthroughs in somatic cell nuclear transfer (SCNT) technology in mammals have raised the possibility of generating potentially unlimited sources of hPSCs for use in research, with potential applications in tissue repair and transplantation medicine.

The differentiated somatic cell genome can be reprogrammed back into an embryonic state when the nucleus is exposed to the molecular milieu of the oocyte cytoplasm via somatic cell nuclear transfer (SCNT). This technique allows for the generation of pluripotent stem cells (pSCs) from terminally-differentiated somatic cells. Because SCNT derived pSCs are autologous to the nuclear donor somatic cells, they are individually patient-specific. This form of autologous transplantation allows transplation of cells into a patient with significantly reduced risk of immune rejection.

Significant advances have been recently achieved in SCNT. Yet, the vast majority of SCNT embryos fail to develop into blastocyst or to term due to undefined reprogramming defects. This includes, for example, aneuploidy and inefficient nuclear reprogramming, leading to high rates of developmental arrest and cell death. It is likely that structural and genotoxic stress during enucleation, reconstruction, along with oocyte activation inefficiencies, and defects during the first mitotic division of the SCNT zygote all contribute to poor development rates using SCNT.

Recent improvements have shed light on the significance of donor nucleus status on SCNT. Nuclear transfer pluripotent stem cells (NT-pSCs) have now been generated using differentiated fetal and infant fibroblasts as nuclear donor. Human NT-hPSCs were subsequently generated from adult and aged patient somatic cells A key observation from these studies is that apparently only high quality oocytes from certain females can support the development of SCNT embryos to the blastocyst stage, thereby indicating a key role for nuclear donor status. Importantly, the existence of such donor variability limits useful oocyte donor pools, and may prevent the full realization of the therapeutic potential for deriving patient-specific NT-hPSCs.

Without being bound by any particular theory, the above studies indicate a key developmental process limitation in SCNT embryos is zygotic gene activation (ZGA). This occurs at 4- to 8-cell stage in large mammals such as pig, bovine and human. Based on the above significance of donor variability, it appears that SCNT embryos have difficulties in ZGA due to undefined epigenetic barriers pre-existing in the genome of donor cells. Dysregulated genes in mouse 2-cell SCNT embryos, and in the late cleavage stage human SCNT embryos have been identified. However, the full nature of the "pre-existing epigenetic barriers" and their relationship with impaired ZGA in SCNT embryos are unknown. Accordingly, there is a need to improve human SCNT cloning efficiency by removing such epigenetic barriers in the genome of the donor cell nuclei so that the human SCNT embryo can proceed efficiently through zygotic gene activation (ZGA) without developmental arrest and successfully develop through the 2-, 4- and 8-cell stage to blastocyst without developmental defects or loss of viability.

The Inventors' prior work has established the utility of applying histone methylation altering agents in order to improve SCNT efficiency by successful ZGA. Namely, the Inventors discovered that CARM1, a member of the protein arginine methyltransferase (PRMT) family, helps establish successful ZGA for blastocyst generation and subsequent NT-hPSC derivation. CARM1 methylates histone H3 on arginine residues 2, 17, and 26 and regulates transcription by the methylation of arginine residues in transcriptional coactivators such as p300/CBP. By altering gene expression profiles by methylating the arginine residues of histones and other proteins that are important for transcription, methylation altering agents such as CARM1 is a very important factor to enhance the efficiency of SCNT and the quality of SCNT embryos and establishes the principle of altering nuclear donor status to remove epigenetic barriers, allow for ZGA and improve SCNT efficiency via increased blastocyst formation. Further details are provided in U.S. App. No. 61/765,548, 62/247,903, 14/180,825 and PCT App. No. PCT/M2014/000160, which are fully incorporated by reference herein Subsequently, it has also been reported that methylation of another histone H3 site, H3K9me3, also serves as a barrier in human SCNT reprogramming. This approach has potentially expanded the usability of human oocyte donors for human SCNT (hSCNT) and confirms that histone demethylase-assisted SCNT can be used in a method for improving human SCNT for therapeutic cloning and production of human nuclear-transfer NT-hPSCs Based on the above, it appears that reprogramming resistant regions (RRRs) in human donor genetic material is enriched for repressive histone modification. Removal of an epigenetic mark in human donor somatic cells can occur through increasing expression or exogenously administering specific histone altering agents. This includes demethylases, including for example, histone methyltransferases (e.g., CARM1) and/or knocking-down or inhibiting a specific histone methyltransferases (e.g., human SUV39h1 or human SUV39h2) in oocytes or in an activated SCNT embryo. Other identified RRRs included epigenetic modifications that are normally associated with active transcription, including H3K27 acetylation, H3K4 methylation, H4K20me1, H3K36me3 and H3K79me3, are significantly enriched in human fibroblast cells, thereby providing other opportunities to eliminate reprogramming barriers.

In human somatic donor nuclei, histone alterations attenuate the ZGA defects in the human donor nuclei and reactivates RRRs, and greatly improves the efficiency of human SCNT (e.g., increases the % of SCNT embryos developing to 2-cell, 4-cell and 8-cell or blastocyst stage). Thus, the Inventors have discovered the "epigenetic barriers" of human SCNT that otherwise stymied successful SCNT. Inhibition and/or removal of the methylation of histones can be applied in in either the nuclei of the human somatic donor cell, the recipient human oocyte, or the human SCNT embryo to significantly improve human SCNT cloning efficiency.

Histones.

It is now known that transcription of genetic information encoded in DNA is in part regulated by chemical modifications to histone proteins. Together with similar modifications such as DNA methylation, these features are part of the epigenetic code regulating gene expression. Histones associate with DNA to form nucleosomes, which themselves bundle to form chromatin fibers, which in turn make up the more familiar chromosome. Histones are globular proteins with a flexible N-terminus (taken to be the tail) that protrudes from the nucleosome. Many of the histone tail modifications correlate very well to chromatin structure and both histone modification state and chromatin structure correlate well to gene expression levels. Chromatin's core structure, the nucleosome, is composed of 146 bp of DNA wrapped around an octamer of histone proteins (H3, H4, H2A and H2B). A number of post-translational modifications to the nucleosome, mostly in histone N-terminal tails, have been described, including methylation, acetylation, phosphorylation and ubiquitination. These covalent modifications define the functional state of chromatin via both cis and trans mechanisms. Cis mechanisms, best typified by acetylation/deacetylation, result in changes to nucleosome packing that increase or decrease DNA accessibility. In trans mechanisms, non-histone proteins that possess particular binding domains recognize specific histone modifications and recruit additional factors that regulate chromatin structure. Together, cis and trans mechanisms embellish the chromatin fiber to generate biological effects that extend beyond the DNA sequence alone.

A significant role for histone state in nuclear transfer find roots in earlier animal studies establishing nuclear transfer approaches, such as mouse. For example, histone deacetylase inhibitors (HDACi) such as trichostatin A (TSA) have been additives observed to improve cloning efficiency, but via a unknown mechanism. Without being bound by any particular theory, it is thought that it can induce hyperacetylation of the core histones, resulting in structural changes to chromatin that permit transcription and enhanced DNA demethylation of the somatic cell-derived genome after SCNT, which is a necessary part of genetic reprogramming. This is affirmed by reports demonstrating HDACi treatment to improve histone acetylation, nascent mRNA production and gene expression in a manner similar to that in normally fertilized embryos. However, how histone methylation is modified in TSA-treated cloned embryos is not completely understood. It has been reported that TSA treatment caused an increase in chromosome decondensation and nuclear volume in SCNT-generated embryos, similar to embryos produced by intracytoplasmic sperm injection. Histone acetylation was increased in parallel with chromosome decondensation. This was associated with a more effective formation of DNA replication complexes in treated embryos.

These initial observation indicate oocyte cytoplasm contains reprogramming mechanisms such as histone acetylation or DNA demethylation that convert the sperm and oocyte nuclei to a totipotent state. However, it is not clear whether endogenous oocyte reprogramming factors are sufficient to reprogram the somatic cell nucleus, because the potential reprogramming machinery of the oocyte cytoplasm is prepared for the receipt of a gametic nucleus, not a somatic cell nucleus. It is likely that incomplete reprogramming of somatic cell nuclei following SCNT arises from poor reprogramming in the oocyte.

These earlier animal studies are extended by affirmed by the more recent human nuclear transfer results. The aforementioned H3K9me3 is highly correlated with constitutive heterochromatin, the condensed, transcriptionally inactive state of chromatin. Other identified RRRs include H3K27 acetylation, H3K4 methylation, H4K20me1, H3K36me3 and H3K79me3, which have been described as involved in transcriptional activation of a variety of homeostatic and developmental processes. Generally speaking, it has been reported that methylation on H3K4, H3K36 and H3K79 for example is considered to be activating whereas methylated H3K9, H3K27 and H4K20 are regarded to be repressive marks. However, there is considerable potential heterogeneity in these effects, as further outlined below.

In the case of H3K4 methylation, this mark is generally associated with active transcription. H3K4 dimethylation appears to be broadly associated with active and potentially active genes, while H3K4 trimethylation is primarily a mark associated with the start site of transcription. Methylation of this fourth amino acid residue from the N-terminus of histone H3 is one of the most studied histone modifications, and with good reason: it's tightly associated with the promoters of active genes. H4K20me1 is associated with transcriptional activation. The most highly transcribed group of genes tend to have H4K20me1 present in addition to the core group of modifications at active promoters and is important for cell cycle regulation. H3K36me3 may also be involved in defining exons. Exons are enriched in nucleosomes in general, but these nucleosomes are also enriched in certain histone modifications including H3K79, H4K20, and especially H3K36me3. It is believed that this pattern influences alternative splicing in some way, perhaps by signalling effector proteins to mark particular exons for inclusion in the final transcript as they exit the RNAPII complex. H3K79me3 is associated with actively transcribed genes but some others have found this modification is enriched at some silent genes. Such discrepancies suggest that the function of histone methylation might be gene specific and depend upon the recruitment of different trans-acting complexes, or that methylation status might be dynamic and titrated during gene expression by the concerted activity of histone methyltransferases (HMTs) and demethylases (HDMs). Importantly, it is noted that histone alteration is highly plastic involving not only methylation, but acetylation as well. For example, while H3K27 is known as a highly potent site for shutting down transcription, such as trimethylation tightly associated with inactive gene promoters, acetylation of H3K27 appears to be antagonistic to the repression of gene expression, such antagonism perhaps being due to the fact that lysine residue cannot be both simultaneously methylated and acetylated.

Epigenetic Target Altering Agents.

Various epigenetic modifying agents are described in Tables 1-4. Non-limiting examples include histoneacetyltransfer (HAT) proteins, histone deacetylase (HDAC) proteins, lysine demethylase domain proteins, and protein methyl transferase (PMT) domain proteins. As described above, in various studies related to CARM1, lysine demethylase, etc. one can increase expression or exogenously administering specific histone altering agents by any number of known means in the art. This includes for example, injection of the mRNA of the agent of interest, culturing in the presence of exogenously administered agent, etc. Various approaches are outlined in FIG. 1.

TABLE 1

Histoneacetyltransfer (HAT) Proteins

| Target_ID (\|domain #) | Full name | Uniprot_ID | NCBI geneid |
|---|---|---|---|
| ATAT1 | alpha tubulin acetyltransferase 1 | Q5SQI0-1 | 79969 |
| CLOCK | clock homolog (mouse) | O15516-1 | 9575 |
| CREBBP | CREB binding protein | Q92793-1 | 1387 |
| ELP3 | elongation protein 3 homolog (*S. cerevisiae*) | Q9H9T3-1 | 55140 |
| EP300 | E1A binding protein p300 | Q09472-1 | 2033 |
| GTF3C4 | general transcription factor IIIC, polypeptide 4, 90 kDa | Q9UKN8-1 | 9329 |
| HAT1 | histone acetyltransferase 1 | O14929-1 | 8520 |
| KAT2A/GCN5L2 | K(lysine) acetyltransferase 2A | Q92830-1 | 2648 |
| KAT2B/PCAF | K(lysine) acetyltransferase 2B | Q92831-1 | 8850 |
| KAT5/TIP60 | K(lysine) acetyltransferase 5 | Q92993-1 | 10524 |
| MYST1 | K(lysine) acetyltransferase 8 | Q9H7Z6-1 | 84148 |
| MYST2 | K(lysine) acetyltransferase 7 | O95251-1 | 11143 |
| MYST3 | K(lysine) acetyltransferase 6A | Q92794-1 | 7994 |
| MYST4 | K(lysine) acetyltransferase 6B | Q8WYB5-1 | 23522 |
| NCOA1 | nuclear receptor coactivator 1 | Q15788-1 | 8648 |
| NCOA3 | nuclear receptor coactivator 3 | Q9Y6Q9-1 | 8202 |
| TAF1 | TAF1 RNA polymerase II, TATA box binding protein (TBP)-associated factor, 250 kDa | P21675-1 | 6872 |
| TAF1L | TAF1 RNA polymerase II, TATA box binding protein (TBP)-associated factor, 210 kDa-like | Q8IZX4-1 | 138474 |

TABLE 2

Histone deacetylase (HDAC) Proteins

| Target_ID (\|domain #) | Full name | Uniprot_ID | NCBI geneid |
|---|---|---|---|
| HDAC1 | histone deacetylase 1 | Q13547_1 | 3065 |
| HDAC10\|1 | histone deacetylase 10 | Q969S8_1 | 83933 |
| HDAC10\|2 | histone deacetylase 10 | Q969S8_1 | 83933 |
| HDAC10\|1 | histone deacetylase 10 | Q969S8_2 | 83933 |
| HDAC10 | histone deacetylase 10 | Q969S8_5 | 83933 |
| HDAC11 | histone deacetylase 11 | Q96DB2_1 | 79885 |
| HDAC2 | histone deacetylase 2 | Q92769_1 | 3066 |
| HDAC3 | histone deacetylase 3 | O15379_1 | 8841 |
| HDAC4 | histone deacetylase 4 | P56524_1 | 9759 |
| HDAC5 | histone deacetylase 5 | Q9UQL6_1 | 10014 |
| HDAC6\|1 | histone deacetylase 6 | Q9UBN7_1 | 10013 |
| HDAC6\|2 | histone deacetylase 6 | Q9UBN7_1 | 10013 |
| HDAC7 | histone deacetylase 7 | Q8WUI4_1 | 51564 |
| HDAC8 | histone deacetylase 8 | Q9BY41_1 | 55869 |
| HDAC9 | histone deacetylase 9 | Q9UKV0_1 | 9734 |
| SIRT1 | sirtuin 1 | Q96EB6_1 | 23411 |
| SIRT2 | sirtuin 2 | Q8IXJ6_1 | 22933 |
| SIRT3 | sirtuin 3 | Q9NTG7_1 | 23410 |
| SIRT4 | sirtuin 4 | Q9Y6E7_1 | 23409 |
| SIRT5 | sirtuin 5 | Q9NXA8_1 | 23408 |
| SIRT6 | sirtuin 6 | Q8N6T7_1 | 51548 |
| SIRT6 | sirtuin 6 | Q8N6T7_2 | 51548 |
| SIRT6 | sirtuin 6 | Q8N6T7_4 | 51548 |
| SIRT7 | sirtuin 7 | Q9NRC8_1 | 51547 |

TABLE 3

Lysine Demethylase Domain Proteins.

| Target_ID (\|domain #) | Full name | Uniprot_ID | NCBI geneid |
|---|---|---|---|
| JARID2 | jumonji, AT rich interactive domain 2 | Q92833_1 | 3720 |
| JHDM1D | jumonji C domain containing histone demethylase 1 homolog D (*S. cerevisiae*) | Q6ZMT4_1 | 80853 |
| JMJD1C | jumonji domain containing 1C | Q15652_1 | 221037 |
| JMJD5 | jumonji domain containing 5 | Q8N371_1 | 79831 |
| MINA | MYC induced nuclear antigen | Q8IUF8_1 | 84864 |
| NO66 | chromosome 14 open reading frame 169 | Q9H6W3_1 | 79697 |

TABLE 4

Protein Methyl Transferase (PMT) Domain Proteins

| Target_ID (\|domain #) | Full name | Uniprot_ID | NCBI geneid |
|---|---|---|---|
| ASH1L | ash1 (absent, small, or homeotic)-like (*Drosophila*) | Q9NR48_1 | 55870 |
| CARM1 | coactivator-associated arginine methyltransferase 1 | Q86X55_1 | 10498 |
| DOT1L | DOT1-like, histone H3 methyltransferase (*S. cerevisiae*) | Q8TEK3_1 | 84444 |
| EHMT1 | euchromatic histone-lysine N-methyltransferase 1 | Q9H9B1_1 | 79813 |
| EHMT2 | euchromatic histone-lysine N-methyltransferase 2 | Q96KQ7_1 | 10919 |
| EZH1 | enhancer of zeste homolog 1 (*Drosophila*) | Q92800_1 | 2145 |
| EZH2 | enhancer of zeste homolog 2 (*Drosophila*) | Q15910_1 | 2146 |

TABLE 4-continued

Protein Methyl Transferase (PMT) Domain Proteins

| Target_ID (\|domain #) | Full name | Uniprot_ID | NCBI geneid |
|---|---|---|---|
| EZH2 | enhancer of zeste homolog 2 (*Drosophila*) | Q15910_5 | 2146 |
| MDS1 | MDS1 and EVI1 complex locus | Q03112_3 | 2122 |
| MLL | myeloid/lymphoid or mixed-lineage leukemia (trithorax homolog, *Drosophila*) | Q03164_1 | 4297 |
| MLL2 | myeloid/lymphoid or mixed-lineage leukemia 2 | O14686_1 | 8085 |
| MLL3 | myeloid/lymphoid or mixed-lineage leukemia 3 | Q8NEZ4_1 | 58508 |
| MLL4 | — | Q9UMN6_1 | 9757 |
| MLL5 | myeloid/lymphoid or mixed-lineage leukemia 5 (trithorax homolog, *Drosophila*) | Q8IZD2_1 | 55904 |
| NSD1 | nuclear receptor binding SET domain protein 1 | Q96L73_1 | 64324 |
| PRDM1 | PR domain containing 1, with ZNF domain | O75626_1 | 639 |
| PRDM10 | PR domain containing 10 | Q9NQV6_1 | 56980 |
| PRDM11 | PR domain containing 11 | Q9NQV5_1 | 56981 |
| PRDM12 | PR domain containing 12 | Q9H4Q4_1 | 59335 |
| PRDM13 | PR domain containing 13 | Q9H4Q3_1 | 59336 |
| PRDM14 | PR domain containing 14 | Q9GZV8_1 | 63978 |
| PRDM15 | PR domain containing 15 | P57071_1 | 63977 |
| PRDM16 | PR domain containing 16 | Q9HAZ2_1 | 63976 |
| PRDM2 | PR domain containing 2, with ZNF domain | Q13029_1 | 7799 |
| PRDM4 | PR domain containing 4 | Q9UKN5_1 | 11108 |
| PRDM5 | PR domain containing 5 | Q9NQX1_1 | 11107 |
| PRDM6 | PR domain containing 6 | Q9NQX0_1 | 93166 |
| PRDM7 | PR domain containing 7 | Q9NQW5_1 | 11105 |
| PRDM8 | PR domain containing 8 | Q9NQV8_1 | 56978 |
| PRDM9 | PR domain containing 9 | Q9NQV7_1 | 56979 |
| PRMT1 | protein arginine methyltransferase 1 | Q99873_1 | 3276 |
| PRMT2 | protein arginine methyltransferase 2 | P55345_1 | 3275 |
| PRMT3 | protein arginine methyltransferase 3 | O60678_1 | 10196 |
| PRMT5 | protein arginine methyltransferase 5 | O14744_1 | 10419 |
| PRMT6 | protein arginine methyltransferase 6 | Q96LA8_1 | 55170 |
| PRMT7\|1 | protein arginine methyltransferase 7 | Q9NVM4_1 | 54496 |
| PRMT7\|2 | protein arginine methyltransferase 7 | Q9NVM4_1 | 54496 |
| PRMT8 | protein arginine methyltransferase 8 | Q9NR22_1 | 56341 |
| SETD1A | SET domain containing 1A | O15047_1 | 9739 |
| SETD1B | SET domain containing 1B | Q9UPS6_1 | 23067 |
| SETD2 | SET domain containing 2 | Q9BYW2_1 | 29072 |
| SETD3 | SET domain containing 3 | Q86TU7_1 | 84193 |
| SETD4 | SET domain containing 4 | Q9NVD3_1 | 54093 |
| SETD5 | SET domain containing 5 | Q9C0A6_1 | 55209 |
| SETD6 | SET domain containing 6 | Q8TBK2_1 | 79918 |
| SETD6 | SET domain containing 6 | Q8TBK2_2 | 79918 |
| SETD7 | SET domain containing (lysine methyltransferase) 7 | Q8WTS6_1 | 80854 |
| SETD8 | SET domain containing (lysine methyltransferase) 8 | Q9NQR1_1 | 387893 |
| SETDB1 | SET domain, bifurcated 1 | Q15047_1 | 9869 |
| SETDB2 | SET domain, bifurcated 2 | Q96T68_1 | 83852 |
| SETMAR | SET domain and mariner transposase fusion gene | Q53H47_1 | 6419 |
| SMYD1 | SET and MYND domain containing 1 | Q8NB12_1 | 150572 |
| SMYD2 | SET and MYND domain containing 2 | Q9NRG4_1 | 56950 |
| SMYD3 | SET and MYND domain containing 3 | Q9H7B4_1 | 64754 |
| SMYD4 | SET and MYND domain containing 4 | Q8IYR2_1 | 114826 |
| SMYD5 | SMYD family member 5 | Q6GMV2_1 | 10322 |
| SUV39H1 | suppressor of variegation 3-9 homolog 1 (*Drosophila*) | O43463_1 | 6839 |
| SUV39H2 | suppressor of variegation 3-9 homolog 2 (*Drosophila*) | Q9H5I1_1 | 79723 |
| SUV420H1 | suppressor of variegation 4-20 homolog 1 (*Drosophila*) | Q4FZB7_1 | 51111 |
| SUV420H2 | suppressor of variegation 4-20 homolog 2 (*Drosophila*) | Q86Y97_1 | 84787 |
| WHSC1 | Wolf-Hirschhorn syndrome candidate 1 | O96028_1 | 7468 |
| WHSC1L1 | Wolf-Hirschhorn syndrome candidate 1-like 1 | Q9BZ95_1 | 54904 |

Histone methyltransferases can be subdivided into three classes: SET-domain containing lysine methyltransferases, non-SET domain lysine methyltransferases and arginine methyltransferases (PRMTs). Histone methyltransferases transfer methyl groups to lysine and arginine residues of histones, particularly on histones H3 and H4. Methylation of histones makes them more neutral in charge, allowing them to separate slightly from DNA; this loose conformation makes the DNA more easily accessible. Histone methyltransferases can activate gene expression in this manner, as transcription of DNA sequences more loosely wrapped around methylated histones is more likely to occur. However, depending on the histone, this same process can also silence gene transcription, as methylation may block the DNA binding and activation sites for some transcription factors or induce chromatin condensation. Methylation of histones by methyltransferases EZH2 or DOT1L has been reported, for example, as capable of silencing tumor suppressor gene expression of tumor suppressor genes. Inhibitors of these methyltransferases includes DOT1L inhibitors EPZ004777, EPZ5676, or EZH2 inhibitors, EPZ005687, EPZ6438, GSK126, GSK343, sorafenib and sorafenib tosylate.

Generally, methyltransferases can be inhibited by co-substrate analogues. There are three known co-substrate analogues that inhibit a variety of methyltransferases: sinefungin, an antibiotic compound that is structurally similar to S-adenosylmethionine (SAM), the demethylated co-substrate SAH as a feedback inhibitor, and methylthioadenosine. Other inhibitors of lysine methyltransferase include the first identified inhibitor, chaetocin, and Bix-01294, an inhibitor of G9a (KMT1C) with an IC50 of 3 mM. It is selective against SUV39H1 and PRMT1. Compound Bix-01338 was discovered as a rather unselective inhibitor of methyltransferases without selectivity between lysine or arginine methyltransferases with an IC50 of 5 mM for G9a and an IC50 of 6 mM for PRMT1. UNC0224 has been presented as a new inhibitor for the lysine methyltransferase G9a with an IC50 of 15. Inhibitors of histone methyltransferases such as EPZ5676, EPZ005687, and GSK126 also exhibit anticancer chemotherapeutic activity across a variety of in vitro and in vivo cancer models.

Protein arginine methylation is mediated by PRMTs that can be subdivided into two classes: type I methyltransferases catalyse the formation of asymmetrically substituted arginine residues and type II methyltransferases mediate the formation of symmetrically methylated arginine residues. CARM1 shows affinity to proline-glycine-methionine-arginine sequences (so-called PGM motifs). PRMT5 has also been shown to methylate PGM motifs. Co-substrate analogues like sinefungin can be used as inhibitors of arginine methyltransferases (also known as AMIs for arginine methyltransferase inhibitors). AMI-1 was the most potent inhibitor with an IC50 of 9 mM against PRMT1. Inhibitors allantodapsone and stilbamidine induce hypomethylation at H4R3.

Other types of epigenetic targets can also be considered for alteration to improve SCNT efficiency. DNA methyltransferases (DNMTs) predominantly methylate CpG nucleotide sequences on DNA. Three active DNA methyltransferases have been identified in mammals: DNMT1, DNMT3A, and DNMT3B. Typically, methylation of these sequences in promoter regions prevents expression of genes by physically preventing activating transcription factors from binding to DNA. Additionally, methylated DNA can bound by methyl-CpGbinding domain proteins that recruit histone remodeling enzymes; these enzymes can condense chromatin structure, offering another mechanism for suppressing gene expression. In some cancers, this results in decreased expression of tumor suppressor genes and unregulated cell growth. Several compounds inhibit DNA methyltransferase activity, including chlorogenic acid, mithramycin, and azacytidine. Examples include, bisdemethoxycurcumin, decitabine, lomeguatrib, o6-benzylguanine, sorafenib and sorafenib tosylate.

Further, histone deacetylases (HDACs) are responsible for removing acetyl groups from N-acetyl lysine amino acids on histones, making them more positively charged and able to more tightly bind the negatively charged DNA backbone. As a result, DNA structure condenses and genetic transcription is less likely to occur. HDACs can prevent expression of genes important in apoptosis and tumor suppression. HDACs are subdivided into four separate groups based on their localization and function. Class I HDACs (isotypes 1, 2, 3, 8) are primarily found in the nucleus, whereas class II HDACs (isotypes 4, 5, 6, 7, 9, 10) are able to travel through the nuclear membrane and are found in both the nucleus and the cytoplasm. HDAC inhibitors show anticancer benefit when co-administered with other chemotherapeutics, particularly in the treatment of leukemias and lymphomas. Examples of HDAC inhibitors include vorinostat, trichostatin A, phenylbutyrate, and scriptaid. Other examples include apicidin, curcumin, entinostat, isoliquiritigenin, mycophenolic acid, nilotinib, penicillic acid, phenethylisothiocyanate-1-cysteine, sodium butyrate, sorafenib, sorafenib tosylate, tozasertib, tubacin, n-valeric acid, valproic acid na salt, vorinostat (saha).

Other examples are found in Bissinger et al., "Targeting epigenetic modifiers: Inhibitors of histone methyltransferases." *Med. Chem. Commun.* 2010, 1, 114-124 and Arrowsmith et al., "Epigenetic protein families: a new frontier for drug discovery." *Nat Rev Drug Discov.* 2012 Apr. 13; 11(5):384-400, which are fully incorporated herein. It is understood targeting an epigenetic may involve administration of small molecules, but could also involve any number of other means known in the art including for example, siRNA knockdown, antibody administration, etc.

Reprogramming Barriers in iPSC and SCNT.

Interestingly, demethylation of H3K9me3 has been used to increase the efficiency of somatic cell reprogramming (e.g., the generation of induced pluripotent stem cells (iPSCs). There are notable differences that exist regarding the barrier between human SCNT and human iPS reprogramming, such as significant differences in the global epigenetic status of an embryonic stem (ES) cell or an induced pluripotent stem cell as compared to a differentiated somatic cell. Pluripotent ES cells have less epigenetic barriers, (e.g., less methylation, in particular in the reprogramming resistant regions (RRRs)) and therefore the efficiency of SCNT embryos produced when a ES cell nuclei is used as the donor nuclei is very different from the efficiency of SCNT embryos produced when the nuclei from a terminally differentiated somatic cell is used. Nevertheless, observations related to a common "reprogramming" barrier in iPSC and SCNT provides basis for possibly combining the two otherwise discrete approaches.

The above observations are affirmed by observations that the whole repertoire of commonly used reprogramming factors may have small-molecule substitutes to make the overall process more efficient. For examples, two or more reprogrammings factors, small-molecule inhibitors of HDACs, PKMTs or lysine demethylases improve the reprogramming efficiency to a level that is comparable to transduction with all four Yamanaka factors (Oct3/4, Sox2, Klf4, c-Myc). Valproic acid, an HDAC inhibitor, also enables the reprogramming of primary human fibroblasts with two factors, OCT4 and SOX2, without the need for the oncogenes MYC or KLF4. Induced pluripotent stem cells created under these conditions resemble human embryonic stem cells in pluripotency, global gene expression profiles and epigenetic states. It was reported that treatment of CARM1 upregulated the expression of Oct-4, Sox-2 and nanog of adult stem cells. Finally, G9A inhibitor BIX-01294 improved reprogramming efficiency in neural progenitor cells transduced with only OCT3/OCT4 and KLF4. Although distinct, iPSC reprogramming and SCNT appear to contain thematically similar or overlapping mechanisms related to altering epigenetic status of donor nuclear material.

Therefore, it appears one could modify the somatic cell's epigenetic status using the IPS reprogramming factors (e.g., all or some of the Thomson (Oct3/4, Sox2, Nanog, and a different gene Lin28) and/or Yamanaka reprogramming factors). One could fully reprogram terminally differentiated somatic cells to make iPSC cells for nuclear transfer (a process that normally takes 4 weeks) prior to obtaining the donor nuclei for insertion into enuceated oocytes. Alternatively, one can reprogramming the terminally differentiated somatic cells partially, (e.g., 7 to 10 days), performed nuclear transfer, relying upon factors within human oocytes to complete the process. Without being bound by any particular theory, it is possible that such an approach can remove the most onerous RRRs that may exist in terminally differentiated cells by reprogramming towards a complete or partial iPSC-like state, thereby ensuring a minimal number of RRRs when nuclear transfer is performed, and enhancing the probability of successful ZGA for NT-hPSC generation.

Described herein is a method for somatic nuclear transfer (SCNT). In one embodiment, the method for SCNT includes enucleation of an oocyte, transfer of one or more donor nuclei, activation of the reconstructed nuclear transferred oocyte (embryo), and optionally, further culturing into blastocyst, and derivation of pluripotent stem cells (pSCs) from the blastocyst. In other embodiments, this includes isolating one or more donor nucleus for injection into the enucleated oocyte.

In various embodiments, enucleating an oocyte includes removal of a metaphase II (MII) stage egg spindle. In various embodiments, the first polar body (1PBE) is removed. In another embodiment, the method includes denuding the cumulus cells before the completion of maturation. In one embodiment, the oocyte is monitored with real-time, non-UV light based monitoring for 1PBE. In another embodiment, the monitoring occurs in the absence of a staining or labeling agent, such as Hoechst staining. In one embodiment, this includes use of a poloscope, such as a Research Instruments (CRi) Oosight™ imaging system. For example, this can include visualizing the zona pellucida and the spindle complex in the harvested MII oocyte harvested with 545 nm polarized light. In another embodiment, enucleating an oocyte includes use of a contoured micropipette allows for both puncture of an oocyte membrane and removal of a 1PBE from the oocyte. In another embodiment, enucleating an oocyte includes use of a piezoelectric drill. In other embodiments, enucleation is performed in a enucleation medium containing cytochalasin B and optionally, a protein phosphatase inhibitor such as caffeine.

In another embodiment, transfer of a donor nucleus includes use of an agent that alters oocyte cell membrane structure. In one embodiment, enucleating an oocyte trough use of an agent that alters oocyte cell membrane structure includes fusion with a somatic cell. For example, transfer of a donor nucleus may include providing 3-4 donor cells an injection pipette (e.g., 12 um diameter), expelling donor cells in a quantity of solution containing a paramyxovirus or paramyxovirus protein, such as Sendai virus envelope protein. This is followed by retrieving the cells using the injection pipette with a distance (4-5 cell length) separating the donor cells arranged linearly, holding an oocyte with a holding pipette, advancing the injection pipette with donor cells into the oocyte. In various embodiments, advancing the injection pipette includes no disruption of the oolema plasma membrane, and insertion of one nuclear donor cell in the perivitelline space, the space between the zona pellucida and the cell membrane, of an oocyte to contact the nuclear donor cells with the oolema plasma membrane, which sits beneath the zona pellucida. In various embodiments, withdrawal of the pipette does not disturb contact between oolema and donor cell. In various embodiments, the oocytes are further incubated. In various embodiments, the cells are fused 1, 2, 3, 4, 5, 6, 7, 8, 9, 10, 11, 12, 13, 14, 15 or more minutes after the donor cell insertion. In various embodiments, the cells are fused 10 min after the donor cell insertion. Optionally, the above procedures are repeated for cells not successfully fused. In various embodiments, a poloscope, such as Oosight™ imaging system, is used throughout the process.

In one embodiment, transfer of a donor nucleus may include electrical cell manipulation, such as electrofusion. In other embodiments, the method may include isolating the nucleus of a somatic nuclear donor, stem cell nuclear donor, and germ cell nuclear donor. In other embodiments, the method may include isolating a somatic nucleus for SCNT, followed by injection of one or more donor nuclei via pipette or piezoelectric injection. In various embodiments, the donor nuclei is from cells such as skin fibroblasts, white blood cells, hair follicles, or any other somatic cell nuclear donor. In another embodiment, the present invention describes a method including isolation and preparation of a nucleus from a germ cell donor. In different embodiments, isolation of a nucleus includes a tissue biopsy, blood draw, or other means of obtaining a tissue sample, processing this tissue with mechanical disassociation, collagenase digestion, washing, centrifuge-based density gradient separation, and/or culturing with standard culture medium.

In other embodiments, the method may include isolating and/or modifying the nucleus of a somatic nuclear donor, stem cell nuclear donor, and germ cell nuclear donor. In various embodiments, this includes application methylation-altering agents, such as epigenetic chromatin and/or histone modification agents, and/or DNA modification agents. In certain embodiments, this includes any one of the agents described in Tables 1-4, including for example, one or more histoneacetyltransfer (HAT) proteins, histone deacetylase (HDAC) proteins, lysine demethylase domain proteins, and protein methyl transferase (PMT) domain proteins. In certain embodiments, the agents are injected as coding mRNA to enhance expression. In certain embodiments, the agents are exogenous protein introduced, by for example, addition into a culturing medium. In other embodiments, a small interfering RNA (siRNA), small molecule, protein, peptide, or antibody is added in order to target an epigenetic target associated with a reprogramming resistant region (RRR). In some embodiments, this includes application of a siRNA, small molecule, protein, peptide, or antibody capable of altering the function of an agent, wherein the agent confers a repressive transcriptional state on a histone mark. In some instances, such application results in an activated transcriptional state on a histone mark. In certain embodiments, the methylation-altering agents and/or DNA modification are expressed as modified recombinant proteins. For example, CARM1 can be modified with 7× arginine (7R)-cell-penetrating peptides (CPPs), or any other proteins known to one of ordinary skill enhance penetration of proteins and peptides across cellular and nuclear membranes, enhance binding and/or transactivation to DNA.

In other embodiments, the method includes epigenetically reprogramming the nuclear donor cells using transcription factor-based reprogramming with octamer binding transcription factor-4 (Oct-4), sex determining region Y-box-2 (Sox-2), nanog, Kruppel-like factor-4 (Klk-4), MyoD, c-Myc, zinc finger protein-42 (Rex-1/Zfp-42), lefty A, teratocarcinoma-derived growth factor (Tdgf), and/or telomeric repeating binding factor (Terf-1). In various embodiments, the epigenetic reprogramming can completely reprogram the nuclear donor cells akin to induced pluripotent stem cells (iPSCs, a process that takes approximately 3-4 weeks). Alternatively, the reprogramming can be partial, requiring culturing for a more limited period of about 5, 6, 7, 8, 9, 10, 11, 12, 13, 14, 15, 16 days.

In various embodiments, the method includes direct piezoelectric injection, viral injection, liposomal injection, or other methods of intracytoplasmic injection. In various embodiments, the transcription factors may be delivered in the form of mRNA, protein, and/or cellular extracts that can be applied prior to the nuclear transfer to the enucleated oocyte.

In another embodiment, the present invention describes a method of activating a reconstructed nuclear transferred oocyte. In one embodiment, activation of a reconstructed nuclear transferred oocyte includes treating nuclear transfer oocytes in activation medium for 5 min at 37° C., following by washing in cleavage medium. In different embodiments, the activation medium is a HEPES-free medium, protein-free medium, G1 or G2 medium, cleavage medium, cleavage assist medium, IVF medium, blastocyst formation medium, or global human embryo culture medium. In certain embodiments, the activation medium includes a calcium ionophore. In different embodiments, the calcium ionophore is ionomycin, A23187, beauvericin, X-537A, avenaciolide, monomacrocyclic polyethers, or macrobiocyclic compounds or cryptates. In different embodiments, the activation medium includes an alcohol, such as ethanol. In different embodiments, the activation medium includes thimerosal. In various embodiments, the activation medium includes 1, 2, 3, 4, 5, 5 or more µM ionomycin. In other embodiments, the method includes electrical activation of an MII stage oocyte. In one embodiment, electrical activation includes electrical pulse in electrofusion medium. In various embodiments, the electrofusion medium includes 0.1-0.5 M mannitol, 0.01-1 mM MgSO4.7H2O, 0.01-1 mg/ml polyvinyl alcohol, 1-10 mg/ml human serum albumin, 0.005-0.5 mM CaCl2.2H2O). In one embodiment, the electrofusion medium includes 0.3 M mannitol, 0.1 mM MgSO4.7H2O, 0.1 mg/ml polyvinyl alcohol, 3 mg/ml human serum albumin, 0.05 mM CaCl2.2H2O). In one embodiment, activating the reconstructed nuclear transferred oocyte allows chromatin condensation, spindle formation, and chemical activation. In other embodiments, combinations of electrical pulses, optionally followed by 6-DMAP may be applied, for example (2×50 µs DC pulses, 2.7 kV/CM) in 0.25M d-sorbitol buffer and 6-DMAP (2 mM, 4 hours). In other embodiments the various described media, such as HEPES-free medium, protein-free medium, G1 or G2 medium, cleavage medium, cleavage assist medium, IVF medium, blastocyst formation medium, or global human embryo culture medium optionally includes a growth factor such as GM-CSF or IGF1. In various embodiments, the growth factor can be added 1, 2, 3, 4, 5, 6, 7 or more days after nuclear transfer.

In various embodiments, the nuclear transfer oocytes are treated in post-activation medium to complete activation. In different embodiments, activated reconstructed nuclear transferred oocytes are then incubated in post-activation medium. In different embodiments, the post-activation medium is a HEPES-free medium, protein-free medium, G1 or G2 medium, cleavage medium, cleavage assist medium, IVF medium, blastocyst formation medium, or global human embryo culture medium. In different embodiments, the post-activation medium includes 6-DMAP, puromycin, ethanol, cycloheximide (CHX), trichostatin A (TSA), and/or cytochalasin B (CB). In different embodiments, the activated oocytes are incubation in the post-activation medium for less than 30, 30-45, 45-60, 60-90, 90-120, 120-150, 150-180, 180-210, 210-240, 240-270, 300-330, 330-360, 360-390, or more than 390 minutes. In certain embodiments, the activated oocytes are incubated for 240, 300, or 360 minutes. In various embodiments, activation and post-activation steps are performed under reduced oxygen conditions. In certain embodiments, reduced oxygen conditions include about 80-85%, 85-90%. 90-95%, 95% or more N2, about 1%, 2%, 3%, 4%, 5%, 6%, 7%, 8%, 9%, 10% or more O2, and about 1%, 2%, 3%, 4%, 5%, 6%, 7%, 8%, 9%, or 10% or more CO2. In certain embodiments, reduced oxygen conditions include about 90% N2, about 5% O2, and about 5% CO2. In various embodiments, the post-activation medium includes 1, 2, 3, 4, 5, 5 or more mM 6-DMAP in cleavage medium for 1, 2, 3, 4, 5, 5 or more hours, incubated in a temperature such as 37° C. in a gas mixture, such about 90% N2, about 5% O2, and about 5% CO2.

After incubation in post-activation medium, the post-activated oocytes are incubated in a wash medium. In different embodiments, the wash medium is a HEPES-free medium, protein-free medium, G1 or G2 medium, cleavage medium, cleavage assist medium, IVF medium, blastocyst formation medium. In another embodiment, the culture medium does not require serial medium change, such as global human embryo culture medium. In certain embodiments, the wash medium includes TSA. In certain embodiments, the post-activated oocytes are incubated in the wash medium including TSA for 240, 300, or 360 minutes. In one embodiment, the post-activated reconstructed nuclear transferred oocyte is washed, and further cultured. In one embodiment, the post-activated reconstructed nuclear transferred oocyte washed in a 6-DMAP free medium. In other embodiments the various described media, such as HEPES-free medium, protein-free medium, G1 or G2 medium, cleavage medium, cleavage assist medium, IVF medium, blastocyst formation medium, or global human embryo culture medium optionally includes a growth factor such as GM-CSF or IGF1. In various embodiments, the growth factor can be added 1, 2, 3, 4, 5, 6, 7 or more days after nuclear transfer.

In another embodiment, activation and/or post-activation steps includes addition of factors isolated from sperm, derivatives and extracts thereof. In one embodiment, human sperm factors are injected into the activated reconstructed eggs using any of the described injection methods. In one embodiment, human sperm factors are injected into the post-activated reconstructed eggs using any of the described injection methods. In various embodiments, after about one, two, three, or four days, the post-activated reconstructed nuclear transferred oocyte is switched to cleavage medium. In a certain embodiment, after about one day post-activated the reconstructed nuclear transferred oocyte is switched to cleavage medium. In various embodiments, sperm factors include for example, factors from isolating cell proteins present inside or outside of sperm cells. In one embodiment, whole sperm extracts are obtained using detergents and mechanical blending of ejaculated sperm. In another embodiment, whole sperm cell extracts are treated with DNAase I and RNAase. In another embodiment, the crude extract is washed in buffer and centrifugation (20,000 g for 2 hours). In other embodiments, fresh ejaculated human sperm is collected and centrifuge at 900 g for 10 min to remove seminal plasma, followed by resuspension of pellet in Sperm-TALP containing 5 mg/mL bovine serum albumin, and centrifuged at the same setting, followed by removal of supernatant and resuspension of the pellet to a final concentration of $20 \times 10^8$ sperm/mL in nuclear isolation medium ((NIM: 125 mM KCl, 2.6 mM NaCl, 7.8 mM Na2HPO4, 1.4 mM KH2PO4, 3.0 mM EDTA disodium salt; pH 7.45 and centrifuged to remove Sperm-TALP. After Sperm-TALP is removed, resuspension of the pellet to the same volume with NIM containing 1 mM dithiothreitol, 100 mM leupeptin, 100 mM antipain, and 100 mg=mL soybean trypsin inhibitor is followed by four cycles of freezing (5 min per cycle in liquid N2) and thawing (5 min per cycle at 15° C.), with compact sperm pellet formation at 20,000× for 50 min at 2° C. Finally, the resulting supernatant is carefully removed, aliquoted, and kept at −80° C. until use.

In various embodiments, the post-activated reconstructed nuclear transferred oocyte is further cultured into a blastocyst. In one embodiment, the post-activated reconstructed nuclear transferred oocyte is further cultured in SAGE cleavage medium, such as Quinn's medium. In another embodiment, the medium promotes pluripotency, such as 3i medium (Neuro basal medium 50%, DMEM/F-12 50%, N2 supplement 1/200 v/v, B27 supplement 1/100 v/v, 100 mM L-glutamine 1/100 v/v, 0.1M ß-ME 1/1000 v/v, SU5402 (FGFR inhibitor) 2 µM, PD184352 (ERK cascade inhibitor) 0.8 µM, CHIR99021 (GSK3 inhibitor) 3 µM) or modified 3i medium (including PD0325901 (MAPK inhibitor) 0.4 µM). In one embodiment, the further culturing is for 1, 2, 3, 4, 5, 5 or more days. In one embodiment, additional culturing is provided in a culture medium with reprogramming factors and/or methylation-altering agents. This includes, for example, any one of the agents described in Tables 1-4, including for example, one or more histoneacetyltransfer (HAT) proteins, histone deacetylase (HDAC) proteins, lysine demethylase domain proteins, and protein methyl transferase (PMT) domain proteins. In various embodiments, the additional culturing is in G2 medium supplemented with CARM1 for 3 days. For example, CARM1 can each be provided at a concentration in the medium of 0.5, 1, 1.5, 2, 2.5, 3, 3.5, 4, 4.5, 5 or more µg/ml. In some embodiments, CARM1 are each provided at a concentration in the medium at 2 µg/ml. In other embodiments, a small interfering RNA (siRNA), small molecule, protein, peptide, or antibody is added in order to target an epigenetic target associated with a reprogramming resistant region (RRR). In some instances, this includes application of an siRNA, small molecule, protein, peptide, or antibody capable of altering the function of an agent, wherein the agent confers a repressive transcriptional state on a histone mark. In some instances, such application results in an activated transcriptional state on a histone mark.

In various embodiments, further culturing into a blastocyst and derivation of pluripotent stem cells (pSCs) from the blastocyst includes treat a cultured blastocyst with acidic Tyrode's solution to remove zona pellucida (ZP). In various embodiments, treatment is for a few (e.g., 1-5) seconds. In various embodiments, removal of the ZP is followed by wash in Hepes-HTF medium. In various embodiments, isolation of the inner cell mass (ICM) includes discarding trophoblast of the blastocyst. In various embodiments, the ICM cells are plated mouse embryonic feeders (MEFs) which are prepared one day before the plating. In some embodiments, whole blastocysts are plated on MEFs. For example, this method includes denuding the zona pellucida of the blastocyst. In various embodiments, the method includes removal of the zona pellucida of blastocysts with 0.05, 0.1, 0.2, 0.3, 0.4, 0.5, 0.6, 0.7, 0.8, 0.9, or 1% pronase in Hepes-HTF medium. In one embodiment, the method includes removal of the zonae pellucida of blastocysts with 0.5% pronase in Hepes-HTF medium. In another embodiment, the method includes application of pronase in TH3 (SAGE Blastocyst medium), medium for 1-10, 10-20, 20-30, 30-60, 60-120, 120-180, or >180 seconds. In another embodiment, the method includes application of 0.5% pronase in HTF medium for 30-60 seconds. In one embodiment, the blastocyst is derived from a parthenote obtained from parthenogenesis of an oocyte. In one embodiment, the hPSC line is a parthenote-derived human pluripotent hPSC (pn-hPSC) cell line. In another embodiment, the blastocyst is derived from a reconstructed nuclear transferred oocyte obtained from somatic cell nuclear transfer (SCNT) of a donor cell nucleus into a recipient oocyte. In one embodiment, the hPSC line is a somatic cell nuclear transfer human pluripotent hPSC (NT-hPSC) cell line. In another embodiment, the present invention describes a method of immunosurgery, including mechanical dispersion of the inner cell mass (ICM) from trophectodermal cells. In various embodiments, a denuded blastocyst is treated with rabbit anti-human spleen serum for about 10, 20, 25, 30, 35, 40, 45, or 60 minutes at 37° C. In one embodiment, a denuded blastocyst is treated with rabbit anti-human spleen serum for about 30 minutes at 37° C. In one embodiment, the method includes washing the denuded blastocyst with TH3 (SAGE Blastocyst medium), incubation in guinea pig complement reconstructed with HECM-9 (SAGE Blastocyst medium), for 30 min at 37° C. In different embodiments, zonae pellucidae of expanded blastocysts are be removed by brief exposure (45-60 seconds) to 0.5% pronase or acidic Tyrode's solution in TH3 (hepes-HTF) medium. In one embodiment, the method optionally includes mechanical cell dispersion using small bore pipetting or laser assisted hatching method using Zilos-tk Unit (Hamilton Thorne) to separate inner cell mass cells from the trophoectodermal cells.

In one embodiment, the method for SCNT includes enucleation of oocytes, transfer of donor nucleus, activation of a reconstructed nuclear transferred oocyte, and optionally, further culturing into a blastocyst, derivation of pluripotent stem cells (pSCs) from the blastocyst.

In other embodiments, the method may include isolating and/or modifying the nucleus of a somatic nuclear donor, stem cell nuclear donor, and germ cell nuclear donor. In various embodiments, this includes application methylation-altering agents, such as epigenetic chromatin and/or histone modification agents, and/or DNA modification agents. In certain embodiments, this includes any one of the agents described in Tables 1-4, including for example, one or more histoneacetyltransfer (HAT) proteins, histone deacetylase (HDAC) proteins, lysine demethylase domain proteins, and protein methyl transferase (PMT) domain proteins. In certain embodiments, the agents are injected as coding mRNA to enhance expression. In certain embodiments, the agents are exogenous protein introduced, by for example, addition into a culturing medium. In other embodiments, a small interfering RNA (siRNA), small molecule, protein, peptide, or antibody is added in order to target an epigenetic target associated with a reprogramming resistant region (RRR). In some instances, this includes application of an siRNA, small molecule, protein, peptide, or antibody capable of altering the function of an agent, wherein the agent confers a repressive transcriptional state on a histone mark. In some instances, such application results in an activated transcriptional state on a histone mark. In certain embodiments, the methylation-altering agents and/or DNA modification are expressed as modified recombinant proteins. For example, CARM1 can be modified with 7× arginine (7R)-cell-penetrating peptides (CPPs), or any other proteins known to one of ordinary skill enhance penetration of proteins and peptides across cellular and nuclear membranes, enhance binding and/or transactivation to DNA.

In other embodiments, the method includes epigenetically reprogramming the nuclear donor cells using transcription factor-based reprogramming with octamer binding transcription factor-4 (Oct-4), sex determining region Y-box-2 (Sox-2), nanog, Kruppel-like factor-4 (Klk-4), MyoD, c-Myc, zinc finger protein-42 (Rex-1/Zfp-42), lefty A, teratocarcinoma-derived growth factor (Tdgf), and/or telomeric repeating binding factor (Terf-1). In various embodiments, the epigenetic reprogramming can completely reprogram the nuclear donor cells akin to induced pluripotent stem cells (iPSCs, a process that takes approximately 3-4 weeks). Alternatively, the reprogramming can be partial, requiring culturing for a more limited period of about 5, 6, 7, 8, 9, 10, 11, 12, 13, 14, 15, 16 days.

In one embodiment, enucleating an oocyte includes removal of a metaphase II stage egg spindle. In various embodiments, the first polar body (1PBE) is removed. In one embodiment, transfer of a donor nucleus includes providing 3-4 donor cells an injection pipette (e.g., 12 um diameter), expelling donor cells in a quantity of solution containing Sendai virus envelope protein, retrieving the cells using the injection pipette with a distance (4-5 cell length) separating the donor cells arrange linearly, hold an oocyte with a holding pipette, advancing the injection pipette with donor cells into the oocyte. In various embodiments, advancing the injection pipette includes no disruption of the oolema, and insertion of one nuclear donor cell in the perivitelline space to contact the nuclear donor cells with the oolema. In various embodiments, withdrawal of the pipette does not disturb contact between oolema and donor cell. In various embodiments, the oocytes is further incubated. In various embodiments, the cells are fused 10 min after the donor cell insertion. Optionally, the above procedures are repeated for cells not successfully fused. In various embodiments, a poloscope, such as Oosight™ imaging system, is used throughout the process. In other embodiments, enucleation is performed in an enucleation medium containing cytochalasin B and optionally, a protein phosphatase inhibitor such as caffeine. In other embodiments, the method includes use of a proteasome inhibitor, such as MG132. In certain embodiments, the method of SCNT can include, transfer of one more donor nuclei thereafter followed by enucleation of the oocyte.

In one embodiment, activation of a reconstructed nuclear transferred oocyte includes treating a reconstructed nuclear transferred oocyte in activation medium for 5 min at 37° C., following by washing in cleavage medium. In various embodiments, the activation medium includes 5 µM ionomycin. In various embodiments, the nuclear transfer oocytes are treated in post-activation medium to complete activation. In various embodiments, the post-activation medium includes 2 mM 6-DMAP in cleavage medium for 4 hrs at 37° C. in 5% CO2/5% N2/90% N2 atmosphere. In one embodiment, the activated nuclear transfer oocyte is washed, and further cultured. In one embodiment, the post-activated reconstructed nuclear transferred oocyte is washed in a 6-DMAP free medium. In one embodiment, the post-activated reconstructed nuclear transferred oocyte is further cultured in SAGE cleavage medium. In one embodiment, the further culturing is for 2 days. In one embodiment, additional culturing is provided in a culture medium with reprogramming factors and/or methylation-altering agents. This includes, for example, any one of the agents described in Tables 1-4, including for example, one or more histoneacetyltransfer (HAT) proteins, histone deacetylase (HDAC) proteins, lysine demethylase domain proteins, and protein methyl transferase (PMT) domain proteins In various embodiments, the additional culturing is in G2 medium supplemented with CARM1) for 3 days. For example, CARM1 can each be provided at a concentration in the medium of 0.5, 1, 1.5, 2, 2.5, 3, 3.5, 4, 4.5, 5 or more µg/ml. In some embodiments, CARM1 are each provided at a concentration in the medium at 2 µg/ml. In other embodiments, a small interfering RNA (siRNA), small molecule, protein, peptide, or antibody is added in order to target an epigenetic target associated with a reprogramming resistant region (RRR). In some instances, this includes application of an siRNA, small molecule, protein, peptide, or antibody capable of altering the function of an agent, wherein the agent confers a repressive transcriptional state on a histone mark. In some instances, such application results in an activated transcriptional state on a histone mark.

In various embodiments, the activated nuclear transfer oocyte is further cultured into a blastocyst. In various embodiments, further culturing into a blastocyst, and derivation of pluripotent stem cells (pSCs) from the blastocyst includes treat a cultured blastocyst with acidic Tyrode's solution (e.g., pH 2.0) to remove zona pellucida (ZP). In various embodiments, treatment is for a few (e.g., 1-5) seconds. In various embodiments, removal of the ZP is followed by wash in Hepes-HTF medium. In various embodiments, isolation of the inner cell mass (ICM) includes discarding trophoblast of the blastocyst. In various embodiments, the ICM cells are plated mouse embryonic feeders (MEFs) which are prepared one day before the plating. In some embodiments, whole embryos are plated on MEFs. In various embodiments, PSC derivation medium is composed of knockout-DMEM supplemented with serum replacement (5% SR, Invitrogen), FBS (10%, Hyclone), plasmamate (5%), bFGF (32 ng/ml), and human LIF (2000 units/ml, Sigma-Aldrich).

Also described herein is a human pluripotent stem cell line derived from somatic cell nuclear transfer (NT-hPSC). In various embodiments, the NT-hPSC is genetically identical, or nearly identical, to a donor nucleus. In different embodiments, the NT-hPSC cell line contains a normal 46 chromosome, XX/XY karyotype. In different embodiments, the NT-hPSC cell line is capable of forming all three embryonic germ layers. In different embodiments, the NT-hPSC cell line expresses one or more pluripotent markers, pluripotent markers including stage-specific embryonic antigen-4 (SSEA-4), SSEA-3, tumor rejection antigen 1-81 (Tra-1-81), Tra-1-60, octamer binding transcription factor-4 (Oct-4), sex determining region Y-box-2 (Sox-2), nanog, zinc finder protein-42 (Rex-1/Zfp-42), lefty A, teratocarcinoma-derived growth factor (Tdgf), telomeric repeating binding factor (Terf-1), and developmental pluripotency-associated gene 2 (Dppa-2). In different embodiments, the NT-hPSC cell line does not contain a recessive lethality. In different embodiments, the NT-hPSC cell line possesses high alkaline phosphatase (AP) and/or telomerase activity. In different embodiments, the NT-hPSC cell line is capable of forming embryoid bodies in suspension and/or teratomas including cells derived from all three embryonic germ layers in an immunodeficient animal.

Described herein is a method for increasing the efficiency of human somatic cell nuclear transfer (SCNT) including contacting any one of a donor human somatic cell, a recipient human oocyte, a hybrid oocyte (e.g., human enucleated oocyte including donor genetic material prior to fusion or activation) or a human SCNT embryo (i.e., after fusion of the donor nuclei with the enucleated oocyte) with an agent capable of altering the epigenetic state of a nucleus. In various embodiments, the agent alters methylation in the cellular nucleus, thereby increasing the efficiency of human SCNT, e.g., increasing the efficiency of the resultant human SCNT to develop to blastocyst and beyond as compared to a non-treated human SCNT embryo. In various embodiments, this includes any one of the agents described in Tables 1-4, including for example, one or more histoneacetyltransfer (HAT) proteins, histone deacetylase (HDAC) proteins, lysine demethylase domain proteins, and protein methyl transferase (PMT) domain proteins. In certain embodiments, the agents are injected as coding mRNA to enhance expression. In certain embodiments, the agents are exogenous protein introduced, by for example, addition into a culturing medium. In other embodiments, a small interfering RNA (siRNA), small molecule, protein, peptide, or antibody is added in order to target an epigenetic target associated with a reprogramming resistant region (RRR). In some instances, this includes application of an siRNA, small molecule, protein, peptide, or antibody capable of altering the function of an agent, wherein the agent confers a repressive transcriptional state on a histone mark. In some instances, such application results in an activated transcriptional state on a histone mark. For example, RRRs identified include H3K27 acetylation, H3K4 methylation, H4K20me1, H3K36me3 and H3K79me3.

In various embodiments, increasing the efficiency of human somatic cell nuclear transfer (SCNT) includes contacting an SCNT embryo (e.g., after fusion of the human enucleated oocyte with the human genetic material of the donor cell), with the agent at least 5, 10, 20, or 20-28 hours post activation. In various embodiments, the SCNT embryo is at the 1, 2-, 4- or 8-cell stage.

In various embodiments, the method includes contacting the nuclei of a donor human cell, e.g., a terminally differentiated somatic cell, with an agent capable of altering the epigenetic state of a nucleus, thereby increasing the efficiency of the SCNT. In different embodiments, the donor somatic cell, recipient oocyte or SCNT embryo are human cells, e.g., are a human donor cell, a recipient human oocyte or human SCNT embryo.

Accordingly, in all aspects of the invention, the method results in an at least about a 5%, or at least about a 10%, or at least about a 13%, or at least about a 15%, or at least a 30% increase, or at least a 50% increase, or a 50%-80% increase, or a greater than 80% increase in efficiency of human SCNT as compared to human SCNT performed in the absence of an agent. For example, efficiency of pre-implantation development of SCNT embryos increases, development of SCNT embryos to blastocyst stage increases, development of hSCNT embryos to expanded blastocyst stage increases, by at least about a 5%, or 7%, or 10%, or 12% or more than 12% develop to expanded blastocyst stage. In another embodiment, the methods increase the efficiency of development of human SCNT embryos, for example, at least a 3-fold, or at least a 4-fold, or at least a 5-fold, or at least about a 6-fold, or at least about a 7-fold, or at least about a 8-fold or more than 8-fold increase in the successful development to blastocyst stage, as compared to those hSCNT embryos prepared in the absence of an Example 1

General Procedures Related to SCNT

Somatic cell nuclear transfer (SCNT) involves overlapping techniques with parthenogenesis, although the key differences involve the transfer of donor nucleus to recipient oocyte and embryo reconstruction. More specifically, SCNT includes 1) preparation of nuclear donor cells, 2) preparation of human MII stage oocytes, 3) enucleation of oocytes, 4) somatic cell nuclear transfer to the enucleated oocytes, 5) activation of the somatic cell nuclear transferred (reconstructed) eggs, 6) culture of the reconstructed eggs in vitro up to blastocyst stage, and 7) derivation of embryonic stem cell lines from those embryos. Cells derived via this process are somatic cell nuclear transfer human pluripotent stem cells (NT-hPSCs).

Example 2

Methylation Altering Agents

The Inventors hypothesized that methylation altering agents could have significant impact on efficient SCNT by altering donor nucleus status through elimination of reprogramming resistant regions (RRR). To investigate this approach, a candidate histone methyl transfer, CARM1, was provided as an additive during SCNT. Specifically, mRNA was to be injected during 2- or 4-cell stage after SCNT to evaluate possible contribution to increasing the number of ICM (inner cell mass) cells and enhancing the quality of SCNT embryos and enhancing quality of nuclear transfer stem cell lines by studying development rate into blastocyst, counting the number of ICM cells and the distribution of ICM cells in order to deduce the effect of CARM1.

Specifically, mouse embryos obtained from IVF and SCNT were cultured to 2- or 4-cell stage in embryo culture medium (potassium simplex-optimized medium, KSOM; Millipore, Danvers, Mass.) containing 10% SPS (Sage, Trumbull, Conn.). The half of blasomeres in 2- and 4-cell embryos were no injected (control), or injected with 10 pl of water (sham) and mouse CARM1 mRNA by using a microinjection system. Their embryonic development to blastocyst were monitored for more 2-3 days. Also, in order to analyze the effect of CARM1 mRNA on the specification of inner cell mass (ICM) in blastocystes, we performed differential staining for detecting of the ICM and trophectoderrm (TE) cells by using two chromatin-specific fluorochromes with different fluorescent spectra: propidium iodide (Sigma-Aldrich), which enters only cells with damaged cell membranes; and bisbenzimide (Hoechst 33342, Sigma-Aldrich), which passes through both damaged and intact membranes. FIG. 1

At day 2-3 days of embryonic development, the zona pellucida (ZP) was removed from each blastocyst by a brief exposure to acid Tyrode's solution (pH 2.5, Sigma-Aldrich). The ZP-free blastocysts were exposed to a 20% rabbit anti-mouse whole serum (Sigma-Aldrich) for 1 h and washed three times (5 min each) with DPBS (Hyclone) containing 0.1% bovine serum albumin (BSA, Sigma-Aldrich). The blastocysts were placed into a 10% guinea pig complement (Sigma-Aldrich) for 1 h, and then propidium iodide and bisbenzimide were added to the complement solution at final concentrations of 10 µg/ml. The blastocysts were then briefly washed with DPBS containing 0.1% BSA, mounted on slides with coverslips, and then examined under ultraviolet light using an epifluorescence microscope (Axio Imager A2; Carl Zeiss, Jena, Germany). The nuclei of ICM cells were labeled with bisbenzimide and appeared blue under 350 nm, while the nuclei of TE cells were labeled with propidium iodide and appeared red under 535 nm. Blue and red images were merged using Zen software (Carl Zeiss). In addition, immunostaining of Oct4 (a ICM marker) and Cdx2 (a TE marker) was performed to analyze the distribution of ICM cells.

Example 3

Results

The blastocyst formation rates of embryos from three groups (control, sham and CARM1 mRNA-injected groups) did not significantly differ. Even total cell numbers of CARM1 mRNA-injected blastocysts were slightly decreased compared with that of control and sham groups, there was no statistically significant. However, the numbers of ICM cells were higher in blastocysts derived from CARM1 mRNA-injected group compared to that of control and sham blastocysts. In addition, the numbers of Oct4-expressed cells in blastocysts from CARM1 mRNA-injected group were also higher than that of blastocysts derived from control and sham blastocysts.

The above preliminary results were extended in further studies utilizing protein treatment. SCNT oocytes were cultured with protein of CARM1 on third day after formation of fertilized embryo to investigate the influence on the development rate into blastocyst. Specifically, mouse embryos obtained from SCNT were cultured to 8-cell stage in embryo culture medium (potassium simplex-optimized medium, KSOM; Millipore, Danvers, Mass.) containing 10% SPS (Sage, Trumbull, Conn.). And then, 8-cell embryos were cultured at 37° C. and 5% CO2 for 48 h in embryo culture medium with 2 µg/ml CPP-CARM1 recombinant protein or DsRed protein (control—non-functional protein) under mineral oil (Sage). Embryonic development was monitored for a further 2 days. CARM1 or DsRed cDNA was inserted into a pET vector to construct an expression plasmid for CARM1 conjugated to 7× arginine (a cell-penetrating peptide (CPP) domain) and a 6×His-tag. The CPP-CARM1 protein expression vector was transformed into BL21 (DE3) pLysS-competent cells (Stratagene Inc., La Jolla, Calif.). Transformed cells were cultured and induced by 1 mM isopropyl-1-thio-β-D-galactopyranoside (IPTG) for 8 h at 20° C. to produce the CPP-CARM1 or DsRed proteins.

Between CPP-CARM1 and DsRed-treated groups, the quality of SCNT embryos at day 3 was not different. However, after 48 hours of in vitro culture, the blastocyst formation rate was significantly higher in the CPP-CARM1-treated group compared to the DsRed-treated group. From these results, we may suggest that treatment of CPP-CARM1 increased embryonic development up to blastocysts. As shown in Table 1 representing three experiments, the rate was increased averagely about 2.5 times compared to the control groups.

TABLE 1

The effect of Carm1 protein on the cloned mice embryo development

| | Oocytes | Enu. | D.T. * | Fusion § | Fused oocytes | Cultured embryos | 2 cells | Treatment (CARM1, D 3) | No. (%) of developed to BLs † |
|---|---|---|---|---|---|---|---|---|---|
| 1 | 90 | 75 | 64 | 61 | 58 (95.1) | 29 | 25 (86.2) | DsRed | 6 (24) |
| | | | | | | 29 | 26 (89.7) | Carm1 | 12 (46.2) |
| 2 | 110 | 104 | 98 | 96 | 67 (69.7) | 34 | 26 (76.5) | DsRed | 5 (19.2) |
| | | | | | | 33 | 25 (75.8) | Carm1 | 10 (40) |
| 3 | 131 | 105 | 97 | 92 | 67 (72.8) | 24 | 17 (70.8) | DsRed | 2 (11.8) |
| | | | | | | 24 | 17 (70.8) | Carm1 | 4 (23.5) |
| Total | 331 | 284 | 259 | 249 | 217 (87.1) | 87 | 68 (78.2) | DsRed | 13 (14.9) |
| | | | | | | 86 | 68 (79.1) | Carm1 | 26 (38.2) |

\* Donor cell transfer
§: Sendai-virus method
†: Blastocysts (BLs) were calculated from 2 cell cleavaged embryos
Donor cell: Cumulus cell
Activation: Strontium, 5~6 hrs
Culture: KSOM media The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the methods of parthenogenesis, somatic cell nuclear transfer, preparing, isolating, or modifying cells used in the described parthenogenesis or somatic cell nuclear transfer techniques, derivation of pluripotent cell lines from the aforementioned techniques, treatment of diseases and/or conditions that relate to the teachings of the invention, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of increasing the generation of a blastocyst, comprising:
providing an enucleated human oocyte;
generating a nuclear transferred (NT) oocyte by adding at least one nucleus of at least one human donor cell to the enucleated human oocyte;
activating the NT oocyte by incubation in an activation medium to generate an activated NT oocyte;
culturing the activated NT oocyte at the 8-cell stage, in a media comprising CARM1 conjugated to a cell penetrating peptide (CPP) to generate a modified, activated NT oocyte;
wherein said culturing of the activated NT oocyte increases the chance of generating a blastocyst and the rate of successfully generating a blastocyst from the modified, activated NT oocyte is at least 100% greater when compared to the rate of successfully generating a blastocyst from an unmodified, activated NT oocyte;
generating a blastocyst from the modified, activated NT oocyte; and
isolating inner cell mass (ICM) cells from the blastocyst, wherein the ICM cells are capable of further culturing as a NT-hPSC cell line.

2. The method of claim 1, wherein adding the at least one nucleus of at least one donor cell comprises direct injection into the enucleated oocyte.

3. The method of claim 1, wherein adding the at least one nucleus of at least one donor cell comprises somatic cell fusion.

4. The method of claim 3, wherein somatic cell fusion comprises contact of Sendai virus, protein or extract thereof, with the at least one donor cell.

5. The method of claim 1, wherein the at least one donor cell comprises a somatic cell or germ cell.

6. The method of claim 1, wherein the NT oocyte is also incubated in the presence of an additional agent capable of altering epigenetic status selected from the group consisting of histoneacetyltransfer (HAT) proteins, histone deacetylase (HDAC) proteins, lysine demethylase domain proteins, protein methyl transferase (PMT) domain protein and combinations thereof.

7. A method of increasing the generation of a blastocyst comprising:
removing the host nucleus of a human oocyte to generate an enucleated human oocyte;
generating a nuclear transferred (NT) oocyte by adding at least one nucleus of at least one human donor cell to the enucleated human oocyte;
activating the NT oocyte by incubation in an activation medium to generate an activated NT oocyte;

culturing the activated NT oocyte at the 8-cell stage, in a media comprising CARM1 conjugated to a cell penetrating peptide (CPP) to generate a modified, activated NT oocyte;

wherein said culturing of the activated NT oocyte increases the chance of generating a blastocyst and the rate of successfully generating a blastocyst from the modified, activated NT oocyte is at least 100% greater when compared to the rate of successfully generating a blastocyst from an unmodified, activated NT oocyte;

generating a blastocyst from the modified activated NT oocyte; and isolating inner cell mass (ICM) cells from the blastocyst, wherein the ICM cells are capable of further culturing as a NT-hPSC cell line.

8. The method of claim 7, wherein the at least one donor cell is cultured in the presence of Oct3/4, Sox2, Klf4, c-Myc and/or Lin28 for at least 3 weeks.

9. The method of claim 7, wherein the at least one donor cell is cultured in the presence of Oct3/4, Sox2, Klf4, c-Myc and/or Lin28 for less than 3 weeks.

10. The method of claim 1, wherein generating a blastocyst from the modified, activated NT oocyte is at least 150% greater when compared to the rate of successfully generating a blastocyst from the unmodified, activated NT oocyte.

11. The method of claim 1, wherein the CPP is 7x arginine.

12. The method of claim 7, wherein the NT oocyte is also injected with an additional agent capable of altering epigenetic status selected from the group consisting of histoneacetyltransfer (HAT) proteins, histone deacetylase (HDAC) proteins, lysine demethylase domain proteins, protein methyl transferase (PMT) domain protein and combinations thereof.

* * * * *